(12) United States Patent
Bozkurt et al.

(10) Patent No.: US 10,918,624 B2
(45) Date of Patent: Feb. 16, 2021

(54) ANTI-CANCER AZOLE COMPOUNDS

(71) Applicant: Imam Abdulrahman Bin Faisal University, Dammam (SA)

(72) Inventors: Ayhan Bozkurt, Dammam (SA); Firdos Alam Khan, Dammam (SA); Seyda Tugba Gunday Anil, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

(21) Appl. No.: 16/429,642

(22) Filed: Jun. 3, 2019

(65) Prior Publication Data

US 2020/0375952 A1 Dec. 3, 2020

(51) Int. Cl.
| | |
|---|---|
| *A61K 31/4196* | (2006.01) |
| *A61K 31/41* | (2006.01) |
| *A61K 31/4178* | (2006.01) |
| *A61P 35/00* | (2006.01) |
| *C07D 403/12* | (2006.01) |

(52) U.S. Cl.
CPC .......... *A61K 31/4196* (2013.01); *A61K 31/41* (2013.01); *A61K 31/4178* (2013.01); *A61P 35/00* (2018.01); *C07D 403/12* (2013.01)

(58) Field of Classification Search
CPC ............... A61K 31/4196; A61K 31/41; A61K 31/4178; A61P 35/00; C07D 403/12
See application file for complete search history.

(56) References Cited

U.S. PATENT DOCUMENTS 4,684,736 A * 8/1987 Topfl .................... C07D 249/08
548/313.7

FOREIGN PATENT DOCUMENTS

| BE | 903 576 | 5/1986 |
| DE | 2049754 A1 | 4/1971 |
| JP | 59-74547 A | 4/1984 |
| JP | 59/52422 B2 | 12/1984 |
| JP | 6-19067 A | 1/1994 |
| JP | 7-301891 A | 11/1995 |
| JP | 7-301892 A | 11/1995 |
| JP | 2005-308822 A | 11/2005 |
| WO | WO-2007130626 A2 * | 11/2007 .......... C07D 487/04 |

OTHER PUBLICATIONS

IUPAC Compendium of Chemical Terminology—Gold Book 2020; accessed online http://goldbook.iupac.org/about.html; 1 p.*
Mayo Clinic Colon Cancer 2020 https://www.mayoclinic.org/diseases-conditions/colon-cancer/synnptoms-causes/syc-20353669 p. 1-9.*
Beige, K., Advances in treating psoriasis, F1000 Prime Reports, Faculty of 1000 Ltd, 2014. p. 1-8.*
Ghoreschi, K.,Selectivity and therapeutic inhibition of kinases: to be or not to be? (2009) Nature Immunol. 10(4, p. 356-360).*
The American Heritage® Medical Dictionary Copyright, Proliferative enteropathy, 2007, 2004 by Houghton Mifflin Company., p. 1-2; http://medical-dictionary.thefreedictionary.com/proliferative+hemorrhagic+enteropathy; accessed online May 4, 2014.*
WebMD, Psoriasis, Jan. 9, 2012; http://www.webmd.com/skin-problems-and-treatments/psoriasis/psoriasis-prevention;accessed online May 4, 2014.*
NCI, Cancer, Mar. 7, 2014; http://www.cancer.gov/cancertopics/cancerlibrary/what-is-cancer;accessed online May 4, 2014.*
Kaur, R., "Recent developments on 1, 2, 4-triazole nucleus in anticancer compounds: a review." Anti-Cancer Agents in Medicinal Chemistry (Formerly Current Medicinal Chemistry-Anti-Cancer Agents) 16.4 (2016): 465-489.*
Nair, A.B., "A simple practice guide for dose conversion between animals and human." Journal of basic and clinical pharmacy 7.2 (2016): 27.*
Registry Chemical Abstracts Service, Columbus, Ohio, Accession Dates May 5, 2011, Jun. 25, 2008, Aug. 24, 2006, and Aug. 28, 2001, p. 1-2.*
Khalid Hakkou, et al., "Degradable Poly(ester triazole)s Based on Renewable Resources", Journal of Polymer Science, Part A, Polymer Chemistry, vol. 53, No. 21, 2015, pp. 2481-2493.
Josef Klosa, "On the implementation of quinazolone (4) derivatives with alkylene oxides", Journal of Practical Chemistry, vol. 31, No. 1-2, Jan. 1966, pp. 34-40 (Abstract only).
H. K. Gouck, et al., "Studies with Compounds Affecting the Development of House Fly Larvae", United States Department of Agriculture Agricultural Research Service, Aug. 1963, 8 pages.

* cited by examiner

*Primary Examiner* — John M Mauro
(74) *Attorney, Agent, or Firm* — Oblon, McClelland, Maier & Neustadt, L.L.P.

(57) ABSTRACT

Compounds comprising azole moieties are disclosed. The disclosed compounds are shown to have anticancer activity. Also disclosed are pharmaceutical composition of the compounds and method of their use in the treatment of cancer.

8 Claims, 18 Drawing Sheets

ANTI-CANCER AZOLE COMPOUNDS

BACKGROUND OF THE INVENTION

Field of the Invention

The present invention relates to azole compounds useful for the treatment of cancer and other proliferative conditions.

Description of Related Art

The "background" description provided herein is for the purpose of generally presenting the context of the disclosure. All references cited herein are incorporated by reference. Work of the presently named inventors, to the extent it is described in this background section, as well as aspects of the description which may not otherwise qualify as prior art at the time of filing, are neither expressly or impliedly admitted as prior art against the present disclosure.

Azoles are five-membered ring nitrogen containing heterocyclic compounds. The aromatic rings of azoles and their derivatives are electron rich and can bind target to proteins such as receptors [Peng et al. Cuff. Top. Med. Chem., 2013, 13(16), 1%3-2010]. Azoles bind to protein receptors via non-covalent bonds and hydrophobic interactions (Peng et al. 2013). Over the past several years, many chemo-preventive and anticancer molecules have been studied [Mudduluru et al. "Repositioning of drugs for intervention in tumor progression and metastasis: Old drugs for new targets" Drug Resist. Updat., (2016) 26, 10-27; Al-Khodairy et al. "In silico prediction of mechanism of erysolininduced apoptosis in human breast cancer cell lines" Am. J. Bioinformatics Res., 2013, 3(3), 62-71; and Raffia et al. "Recent advanced in bioactive systems containing pyrazole fused with a five membered heterocycle" Eur. J. Med. Chem., 2016, 97, 732-746]. One of the main objectives of the current cancer therapy is to explore new therapeutic molecules that can be easily synthesized at low cost and are better tolerated by patents compared to other drugs currently in use for treatment of cancer. Although there has been significant improvement in treatment and prevention of cancers, the incidence of cancer remains on the increase and cancer is becoming the leading cause of morbidity globally [Wong et al. "Global Incidence and Mortality for Prostate Cancer: Analysis of Temporal Patterns and Trends in 36 Countries" Eur Urol. (2016 November) 70(5):862-874. doi: 10.1016/j.eururo.2016.05.043. Epub 2016 Jun. 8]. Currently used anticancer drugs are directed to specific targets. Since cancer cells have the ability to utilize alternative metabolic pathways to grow, they develop drug resistance [Pathania et al. "Opportunities in discovery and delivery of anticancer drugs targeting mitochondria and cancer cell metabolism" Adv. Drug Deliv. Rev. (2009) 61(14), 1250-1275].

A survey of drug bank databases found that more than a thousand azoles and their derivatives have been reported to have therapeutic effects [Wishart et al. "DrugBank: A comprehensive resource for in silica drug discovery and exploration" Nucleic Acids Res., 2006, 34, (Database issue), D668-672]. Recently, it has been reported that azoles and their derivatives have anticancer properties [Kaur et al. "Recent developments on 1,2,4-triazole nucleus in anticancer compounds: A review. Anticancer Agents Med. Chem." (2016) 16, (4), 465-489; Soares et al. "Chiral 6,7-bis(hydroxymethyl)-1H,3Hpyrrolo[1,2-c]thiazoles with anti-breast cancer properties" Eur. J. Med. Chem. (2013) 60, 254-262; Wang et al. "Design, synthesis and biological evaluation of novel hybrid compounds of imidazole scaffold-based 2-benzylbenzofuran as potent anticancer agents" Eur. J. Med. Chem. (2013) 62, 111-121; Khaybullin et al. "Synthesis and anticancer evaluation of complex unsaturated isosteviol-derived triazole conjugates" Future Med. Chem., 2015, 7(18), 2419-2428; Jabir et al. "Use of azoles containing natural products in cancer prevention and treatment: An overview" Antican. Agents Med. Chem. (2016); Duan et al. "Design and synthesis of novel 1,2,3-triazoledithiocarbamate hybrids as potential anticancer agents" Eur. J. Med. Chem. (2013) 62, 11-19; and Kumar et al. "Pyrazole containing natural products: synthetic preview and biological significance" Eur. J. Med Chem. (2013) 69, 735-753]. Among azole derivatives, 1,2,4-triazole has emerged as an efficacious therapeutic drugs due to its anti-inflammatory and anti-proliferative properties [Tahlan et al. "Synthesis, antimicrobial, anticancer evaluation and QSAR studies of N'-substituted benzylidene/2-hydroxynaphthalen-1-ylmethylene/3-phenylallylidene/5-oxopentylidene-4-(2-oxo-2-(4H-1,2,4-triazol-4-yl) methylamino)benzohydrazides" Arab. J. Chem. 10, S2009-S2017]. It is water soluble and interacts with enzymes involved in cancer pathogenesis [Aliabadi et al. "Design, synthesis and cytotoxicity evaluation of N-(5-Benzylthio)-4H-1,2,4-Triazol-3-YL)-4-fluorobenzamide derivatives as potential anticancer agents" Pharm. Chem. J. 49, 694-699]. Moreover, compounds containing a triazole moiety display anticancer properties [Kommagalla et al. "Optimization of the anticancer activity of phosphatidylinositol-3 kinase pathway inhibitor PITENIN-1: switching a thiourea with 1,2,3-triazole". Medchemcomm" (2014) September; 5(9):1359-1363; and El-Sherief et al. (2018) "Novel 1,2,4-triazole derivatives as potential anticancer agents: design, synthesis, molecular docking and mechanistic studies" Bioorg. Chem. 76, 314-325]. Also, 1,2,4-triazole derivatives have anti-proliferative effects on cancer cell lines [Qin et al. "Design and synthesis of novel 2-(4-(2-(dimethylamino)ethyl)-4H-1,2,4-triazol-3-yl)pyridines as potential antitumor agents" Eur. J. Med. Chem. 81, 47-58]. Other azole derivatives such as 3-aminotriazole, 5-Aminotetrazole, and imidazole are reported to have anticancer properties [Liu et al. "N-aryltriazole ribonucleosides with potent antiproliferative activity against drug-resistant pancreatic cancer" Bioorg Med Chem Lett. (2010 Apr. 15) 20(8):2503-7; Serebryanskaya et al. Synthesis, characterization, and biological evaluation of new tetrazole-based platinum (II) and palladium(II) chlorid complexes-potent cisplatin analogues and their trans isomers. J Inorg Biochem. (2013 March) 120:44-53; and Dvořák et al. "Evaluation of in vitro cytotoxicity of one-dimensional chain [Fe(salen)(L)](n) complexes against human cancer cell lines" Toxicol In Vitro. (2012 April) 26(3):480-4].

U.S. Pat. No. 4,684,736A discloses bisimidazolium salts that include imidazole and 2-alkyl imidazole derivatives having the structure:

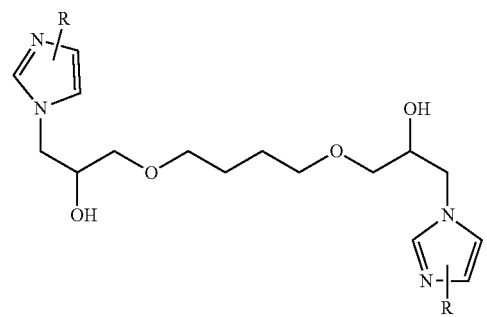

wherein R is methyl, ethyl, —(CH$_2$)$_{10}$CH$_3$, and phenyl as useful compounds as a cellulose dyeing aid. The patent does not disclose any triazole and tetrazole derivatives or the use of any the disclosed compounds as anticancer drugs Due to the various therapeutic benefits of azole derivatives, one objective of the present disclosure is to provide compounds comprising one or more azole moiety conjugates having anticancer and anti-proliferative activity.

SUMMARY OF THE INVENTION

A first aspect of the invention is directed to a compound having the chemical formula A(BC)$_n$ or a salt thereof, a solvate, a tautomer thereof, a stereoisomer thereof, or a mixture thereof, wherein:

A is optionally substituted linear or branched carbon chain having 2 to 12 carbon atoms, an optionally substituted carbocyclic ring having 4 to 6 carbon atoms, an optionally substituted aromatic ring, optionally substituted biphenyl, or HO—(CHR$_1$CH$_2$O)$_x$H, wherein R$_1$ is hydrogen, methyl or ethyl and x is an integer in the range of 2 to 10, B is a linking functionality selected from the group consisting of ether, thioether, amino, amido, sulfonamide, carbamate, and urea, C is an azole containing moiety, and n is an integer in the range of 1 to 6;

with the proviso that A, B, and C are not —CH$_2$CH$_2$CH$_2$CH$_2$—, oxygen and —CH$_2$CH(OH)CH$_2$-imidazole, respectively, wherein the imidazole is optionally substituted with methyl or ethyl group.

In a preferred embodiment, A is —CH$_2$CH$_2$CH$_2$CH$_2$—

In another preferred embodiment, B is oxygen.

In another preferred embodiment, C is —CH$_2$CH(OH)—CH$_2$-Azole.

In another preferred embodiment, n equals 2.

In another preferred embodiment, the azole is selected from the group consisting of:

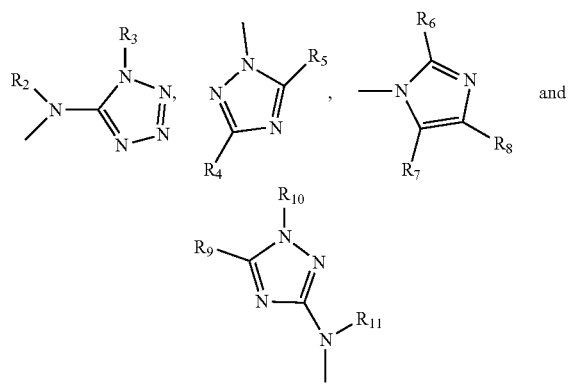

wherein R$_2$, R$_3$, R$_4$, R$_5$, R$_6$, R$_7$, R$_8$, R$_9$, R$_{10}$, and R$_{11}$ are independently selected from the group consisting of a hydrogen, NR$_{12}$R$_{13}$, OR$_{12}$, SR$_{12}$, SeR$_{12}$, an optionally substituted alkyl, an optionally substituted alkylene, an optionally substituted cycloalkyl, an optionally substituted aryl, and an optionally substituted arylalkyl; and R$_{12}$ and R$_{13}$ are independently hydrogen, an optionally substituted alkyl, an optionally cycloalkyl, an optionally substituted heterocyclyl, an optionally substituted aryl, and an optionally substituted arylalkyl; or R$_2$ and R$_3$, R$_7$ and R$_8$, or R$_9$ and R$_{10}$ are linked together forming an optionally substituted ring selected from the group consisting of a five membered ring, a six membered ring, a seven membered ring, or an eight membered ring.

In a more preferred embodiment, R$_2$, R$_3$, R$_4$, R$_5$, R$_6$, R$_7$, R$_8$, R$_9$, R$_{10}$, and R$_{11}$ are hydrogens.

In another preferred embodiment, the compound has the chemical structure of formula I:

Formula I

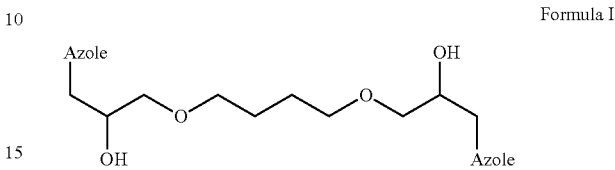

In more preferred embodiment, the azole is selected from the group consisting of:

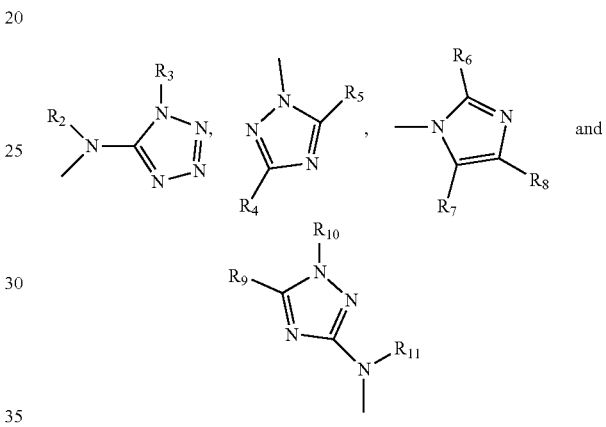

wherein R$_2$, R$_3$, R$_4$, R$_5$, R$_6$, R$_7$, R$_8$, R$_9$, R$_{10}$, and R$_{11}$ are independently selected from the group consisting of a hydrogen, NR$_{12}$R$_{13}$, OR$_{12}$, SR$_{12}$, SeR$_{12}$, an optionally substituted alkyl, an optionally substituted alkylene, an optionally substituted cycloalkyl, an optionally substituted aryl, and an optionally substituted arylalkyl; and R$_{12}$ and R$_{13}$ are independently hydrogen, an optionally substituted alkyl, an optionally cycloalkyl, an optionally substituted heterocyclyl, an optionally substituted aryl, and an optionally substituted arylalkyl; or R$_2$ and R$_3$, R and R$_8$, or R$_9$ and R$_{10}$ are linked together forming an optionally substituted ring selected from the group consisting of a five membered ring, a six membered ring, a seven membered ring, or an eight membered ring.

In the most preferred embodiment, R$_2$, R$_3$, R$_4$, R$_5$, R$_6$, R$_7$, R$_8$, R$_9$, R$_{10}$, R$_{11}$ are hydrogens.

A second aspect of the invention is directed to pharmaceutical composition comprising the compound of the invention, and a pharmaceutically acceptable carrier and/or excipient.

In a preferred embodiment, the pharmaceutical composition comprises 0.1-400 µM of the compound of the invention relative to the total volume of the composition.

In another preferred embodiment, the pharmaceutically acceptable carrier and/or excipient is at least one selected from the group consisting of a buffer, an inorganic salt, a fatty acid, a vegetable oil, a synthetic fatty ester, a surfactant, and a polymer.

In another preferred embodiment, the pharmaceutical composition further comprises at least one chemotherapeutic agent.

A third aspect of the invention is directed to a method of treating a proliferative disorder comprising administering to a subject in need of therapy a sufficient amount of a pharmaceutical composition comprising a chemical compound having the formula A(BC)$_n$ or a salt thereof, a solvate, a tautomer thereof, a stereoisomer thereof, or a mixture thereof, wherein:

A is optionally substituted linear or branched carbon chain having 2 to 12 carbon atoms, an optionally substituted carbocyclic ring having 4 to 6 carbon atoms, an optionally substituted aromatic ring, optionally substituted biphenyl, or HO—(CHR$_1$CH$_2$O)$_x$H, wherein R$_1$ is hydrogen, methyl or ethyl and x is an integer in the range of 2 to 10, B is a linking functionality selected from the group consisting of ether, thioether, amino, amido, sulfonamide, carbamate, and urea, C is an azole containing moiety, and n is an integer in the range of 1 to 6.

In a preferred embodiment of the method, A is —CH$_2$CH$_2$CH$_2$CH$_2$—.

In a preferred embodiment of the method, B is oxygen.

In a preferred embodiment of the method, C is —CH$_2$CH(OH)—CH$_2$-Azole.

In another preferred embodiment of the method, the azole is selected from the group consisting of:

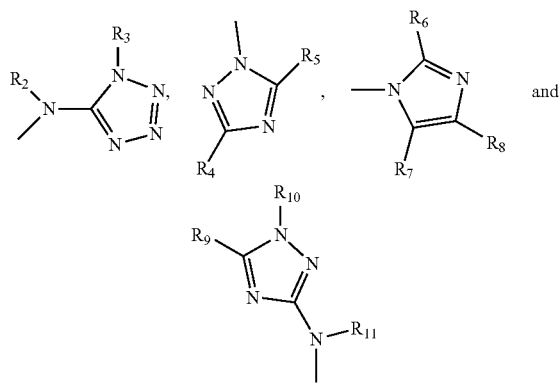

wherein R$_2$, R$_3$, R$_4$, R$_5$, R$_6$, R$_7$, R$_8$, R$_9$, R$_{10}$, and R$_{11}$ are independently selected from the group consisting of a hydrogen, NR$_{12}$R$_{13}$, OR$_{12}$, SR$_{12}$, SeR$_{12}$, an optionally substituted alkyl, an optionally substituted alkylene, an optionally substituted cycloalkyl, an optionally substituted aryl, and an optionally substituted arylalkyl; and R$_{12}$ and R$_{13}$ are independently hydrogen, an optionally substituted alkyl, an optionally cycloalkyl, an optionally substituted heterocyclyl, an optionally substituted aryl, and an optionally substituted arylalkyl; or R$_2$ and R$_3$, R$_7$ and R$_8$, or R$_9$ and R$_{10}$ are linked together forming an optionally substituted ring selected from the group consisting of a five membered ring, a six membered ring, a seven membered ring, or an eight membered ring.

In a preferred embodiment, the proliferative disorder is cancer.

In a more preferred embodiment, the cancer is at least one selected from the group consisting of ovarian cancer, cervical cancer, testicular cancer, colon cancer, rectal cancer, bladder cancer, breast cancer, non-small cell lung cancer, esophageal cancer, endometrial cancer, head and neck cancer, and osteogenic sarcoma.

In another preferred embodiment, the subject is a mammal.

In another preferred embodiment, the subject is human.

In another preferred embodiment, the subject in need of therapy has a central nervous system tumor or a germ cell tumor.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1A:
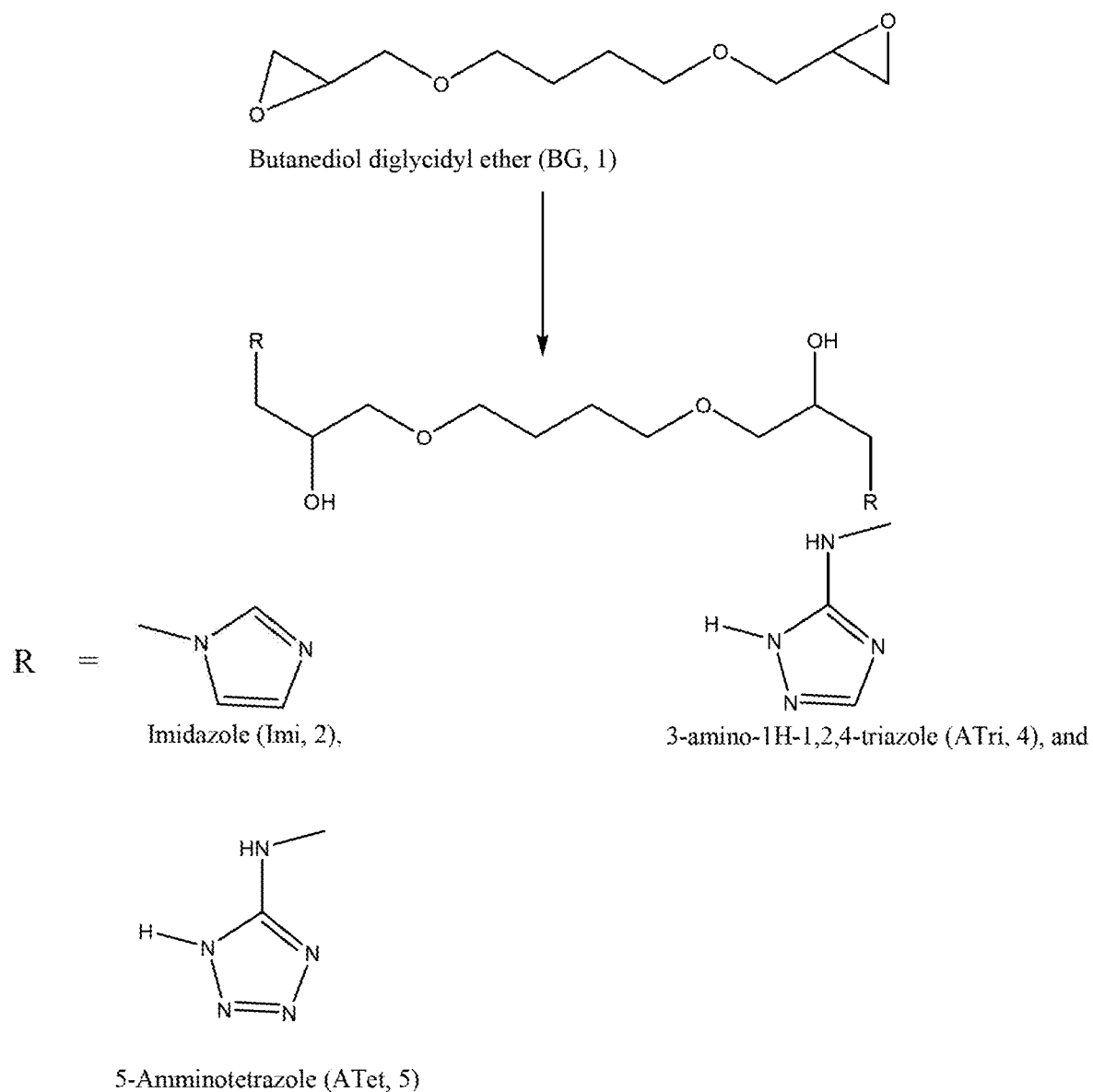
FIG. 1A shows the chemical structure of 1,4-butanediol diglycidyl ether (BG, 1) and BG-azole conjugates of imidazole (2), 1,2,4-Triazole (3), 3-Amino-1H-1,2,4-triazole (4), and 5-aminotetrazole (5).

Embodiments of the present disclosure will now be described more fully hereinafter with reference to the accompanying drawings, in which some, but not all embodiments of the disclosure are shown. The present disclosure will be better understood with reference to the following definitions.

All publications mentioned herein are incorporated herein by reference in full for the purpose of describing and disclosing the methodologies, which are described in the publications, which might be used in connection with the description herein. Nothing herein is to be construed as an admission that the inventors are not entitled to antedate such disclosure by virtue of prior disclosure. Also, the use of "or" means "and/or" unless stated otherwise. Similarly, "comprise," "comprises," "comprising," "include," "includes," and "including" are interchangeable and not intended to be limiting.

Unless otherwise specified, "a" or "an" means "one or more".

As used herein, the term "about" refers to an approximate number within 20% of a stated value, preferably within 15% of a stated value, more preferably within 10% of a stated value, and most preferably within 5% of a stated value. For example, if a stated value is about 8.0, the value may vary in the range of 8±1.6, ±1.0, ±0.8, ±0.5, ±0.4, ±0.3, ±0.2, or ±0.1.

As used herein, the terms "compound" and "complex" are used interchangeably, and are intended to refer to a chemical entity, whether in a solid, liquid or gaseous phase, and whether in a crude mixture or purified and isolated.

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, isopropanol, n-butanol, isobutanol, tert-butanol, ethyl acetate and other lower alkanols, glycerine, acetone, dichloromethane (DCM), dimethyl sulfoxide (DMSO), dimethyl acetate (DMA), dimethyl formamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g. polyethylene glycol (PEG), polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those skilled in the art.

As used herein, the term "tautomer" refers to constitutional isomers of organic compounds that readily convert by tautomerization or tautomerism. The interconversion commonly results in the formal migration of a hydrogen atom or proton, accompanied by a switch of a single bond and adjacent double bond. Tautomerism is a special case of structural isomerism, and because of the rapid interconversion, tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic tautomerism in heterocyclic rings), enamine and enamine and anomers of reducing sugars.

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection of their order differs. By definition, molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans- (E- and Z-) isomers, and non-enantiomeric optical isomers. Diastereomers seldom have the same physical properties. In terms of the present disclosure, stereoisomers may refer to enantiomers, diastereomers, or both.

Conformers, rotamers, or conformational isomerism refers to a form of isomerism that describes the phenomenon of molecules with the same structural formula but with different shapes due to rotations around one or more bonds. Different conformations can have different energies, can usually interconvert, and are very rarely isolatable. There are some molecules that can be isolated in several conformations. Atropisomers are stereoisomers resulting from hindered rotation about single bonds where the steric strain bather to rotation is high enough to allow for the isolation of the conformers. In terms of the present disclosure, stereoisomers may refer to conformers, atropisomers, or both.

In terms of the present disclosure, stereoisomers of the double bonds, ring systems, stereogenic centers, and the like can all be present in the compounds, and all such stable isomers are contemplated in the present disclosure. Cis- and trans- (or E- and Z-) stereoisomers of the compounds of the present disclosure wherein rotation around the double bond is restricted, keeping the substituents fixed relative to each other, are described and may be isolated as a mixture of isomers or as separated isomeric forms. S- and R- (or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example, by chromatography, fractional crystallization, or use of a chiral agent.

In addition, the present disclosure is intended to include all isotopes of atoms occurring in the present compounds and complexes. Isotopes include those atoms having the same atomic number but different mass numbers. By way of general example, and without limitation, isotopes of hydrogen include deuterium and tritium. Isotopes of carbon include $^{13}C$ and $^{14}C$. Isotopes of nitrogen include $^{14}N$ and $^{15}N$. Isotopes of oxygen include $^{16}O$, $^{17}O$ and $^{18}O$. Isotopically-labeled compounds of the disclosure may generally be prepared by conventional techniques known to those skilled in the art or by processes analogous to those described herein, using an appropriate isotopically-labeled reagent in place of the non-labeled reagent otherwise employed.

As used herein, the term "substituted" refers to at least one hydrogen atom that is replaced with a non-hydrogen group, provided that normal valences are maintained and that the substitution results in a stable compound. When a substituent is noted as "optionally substituted", the substituents are selected from the exemplary group including, but not limited to, halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanylamino, aroylamino, aralkanoylamino, substituted alkanoylamino, substituted arylamino, substituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamide (e.g. —$SO_2NH_2$), substituted sulfonamide, nitro, cyano, carboxy, carbamyl (e.g. —$CONH_2$), substituted carbamyl (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof and the like.

As used herein, the term "alkyl" unless otherwise specified refers to both branched and straight chain saturated aliphatic primary, secondary, and/or tertiary hydrocarbons of typically $C_1$ to $C_{10}$, preferably $C_1$ to $C_6$, more preferably $C_2$ to $C_3$, and specifically includes, but is not limited to, methyl, trifluoromethyl, ethyl, n-propyl, isopropyl, n-butyl, sec-butyl, isobutyl, t-butyl, pentyl, isopentyl, neopentyl, hexyl, isohexyl, 3-methylpentyl, 2,2-dimethylbutyl, and 2,3-dimethylbutyl.

As used herein, the term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

The term "alkenyl" refers to a straight, branched, or cyclic hydrocarbon fragment containing at least one C=C double bond. Exemplary alkenyl groups include, without limitation, 1-propenyl, 2-propenyl (or "allyl"), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, and 9-decenyl.

The term "alkynyl" refers to a straight or branched hydrocarbon fragment containing at least one C≡C triple bond. Exemplary alkynyl groups include, without limitation, ethynyl, 1-propynyl, 2-propynyl (i.e., propargyl), 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonynyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, and 9-decynyl.

The term "alkoxy" refers to a straight or branched chain alkoxy including, but not limited to, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy, and decyloxy.

As used herein, the term "aryl" unless otherwise specified refers to functional groups or substituents derived from an aromatic ring including, but not limited to, phenyl, biphenyl, napthyl, anthracenyl, thienyl, and indolyl.

The term "arylalkyl", as used herein, refers to a straight or branched chain alkyl moiety having 1 to 8 carbon atoms that is substituted by an aryl group as defined herein, and includes, but is not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

The term "alkanoyl", as used herein, refers to an alkyl group of specified number of carbon atoms that is bound to an oxygen atom through a double bond. Exemplary alkanoyl groups include, but are not limited to, formyl, acetyl, propanoyl, butyryl, and hexanoyl.

The term "aroyl" as used in this disclosure refers to an aromatic carboxylic acyl group includes, for example, benzoyl, 1-naphthoyl, and 2-naphthoyl.

The term "halogen", as used herein, means fluorine, chlorine, bromine, and iodine.

A first aspect of the invention is directed to a compound having the chemical formula $A(BC)_n$, or a salt thereof, a solvate, a tautomer thereof, a stereoisomer thereof, or a mixture thereof, wherein:

A is optionally substituted linear or branched carbon chain having 2 to 12 carbon atoms, an optionally substituted carbocyclic ring having 4 to 6 carbon atoms, an optionally substituted aromatic ring, optionally substituted biphenyl, or $HO-(CHR_1CH_2O)_xH$, wherein $R_1$ is hydrogen, methyl or ethyl and x is an integer in the range of 2 to 10, B is a linking functionality selected from the group consisting of ether, thioether, amino, amido, sulfonamide, carbamate, and urea, C is an azole containing moiety, and n is an integer in the range of 1 to 6;

with the proviso that A, B, and C are not $-CH_2CH_2CH_2CH_2-$, oxygen, and $-CH_2CH(OH)CH_2-$ imidazole, respectively, wherein the imidazole is optionally substituted with methyl or ethyl group.

As used herein A in the formula $A(BC)_n$ is an organic moiety optionally substituted or unsubstituted carbon chain containing 2-12 carbon atoms, an optionally substituted carbocyclic ring having 4 to 6 carbon atoms, an optionally substituted aromatic ring, optionally substituted biphenyl or $HO-(CHR_1CH_2O)_xH$, wherein $R_1$ is hydrogen, methyl or ethyl and x is an integer in the range of 2 to 10. The carbon chain may be saturated or unsaturated linear or branched and having 2 to 12 carbon atoms. In some embodiments, the carbon chain is flexible saturated linear carbon chain having the formula $(CH_2)_n$, wherein n is an integer in the range of 2-12, preferably 2-8, preferably 3-6, and preferably 3-5. In a particularly preferred embodiment, the carbon chain is $(CH_2)_4$. In some other embodiments, the conformation of the carbon chain may be restricted by introducing one or more double or triple bonds into the carbon chain. Examples of unsaturated carbon chains include, but are not limited to $-CH_2-CH=H-$ cis- and trans-$CH_2-CH=CH-CH_2-$, cis- and trans-$(CH=CH)_n-$, $H_2C-C\equiv C-$, $H_2C-C\equiv C-CH_2$ or $-(C\equiv C)n-$, wherein n is an integer in the range of 1-3.

In some embodiments, A is an optionally substituted four, five, or six membered carbocyclic ring. In some other embodiments, A is an optionally substituted phenyl or biphenyl moiety. In other embodiments, A is an aromatic ring such as, but not limited to phenyl, naphthyl, biphenyl, and heteroaromatic rings such as, but not limited to a pyridine ring, a furan ring, a pyrrole, a thiophene, an imidazole ring, and the like.

In some embodiments, A and B in formula $A(BC)_n$ are an oligomer having the formula $-O-(CHR_1CH_2O)_n$ wherein $R_1$ is a hydrogen or an alkyl group such as but not limited to methyl, ethyl, or propyl, and n is an integer in the range 2 to 20, preferably 3-15, more preferably 4-10, most preferably 2-8. The oligomer may be a homo-oligomer or hetero-oligomer. In a more preferred embodiment, the oligomer is that of ethylene glycol or propylene glycol. Both oligo ethylene glycol and propylene glycol are water soluble and known to be biocompatible and do not trigger undesired immune response.

As used herein B in formula $A(BC)_n$ is a linking moiety of A and C. Such linking moieties include, but are not limited to, $-O-$, $-S-$, $-NH-$, $-CONH-$, $-SO_2NH-$, $-OCONH-$, and $-NHCONH-$.

As used herein the term "azole" referrers to a class of five-membered heterocyclic aromatic compounds containing a nitrogen atom and at least one other non-carbon atom such as but not limited to nitrogen, oxygen, and sulfur as part of the ring. The aromatic ring of the azoles contains two double bonds and one lone pair of electrons from a heteroatom that give the ring six electrons to satisfy aromaticity. The numbering of ring atoms in azoles starts with the heteroatom that is not part of a double bond, and then proceeds towards the other heteroatom. Examples of nitrogen-only containing azoles include, but are not limited to, imidazole, pyrazole, 1,2,3-triazole, 1,2,4trazole, and tetrazole. Oxygen containing azoles include oxazole, isoxazole, 1,2,4-oxadiazole, 1,2,5-oxadiazole, and 1,3,4-oxadiazole. Sulfur containing azoles include, but are not limited to thiazole, isothiazole, 1,2,3-thiadiazole, 1,2,4-thiadiazole, 1,2,5-thiazole, and 1,3,4-thiazole. The compounds of the present disclosure comprise one or more organic moiety B containing an optionally substituted azole.

The organic moiety C in a compound of formula $A(BC)_n$ has an optionally substituted carbon chain of at least three, four, five, or six carbon atoms or an aromatic ring and at least one azole ring covalently bonded to one of the carbon atoms. The carbon chain may be saturated or unsaturated. In some embodiments the carbon chain is substituted with one or more substituents such as, but not limited to, alkyl, aryl, heteroaryl, hydroxyl, and/or alkoxy. In some embodiments, the azole ring is covalently bonded to the carbon chain through a ring nitrogen atom of the azole ring or through a substituent on the ring such as amino substituent, hydroxyl substituent, or a thiol substituent.

In some embodiments, the azole is selected from the group consisting of:

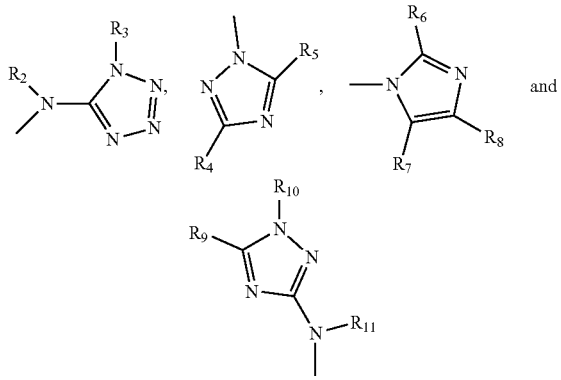

wherein $R_2$, $R_3$, $R_4$, $R_5$, $R_6$, $R_7$, $R_8$, $R_9$, $R_{10}$, and $R_{11}$ are independently selected from the group consisting of a hydrogen, $NR_{12}R_{13}$, $OR_{12}$, $SR_{12}$, $SeR_{12}$, an optionally substituted alkyl, an optionally substituted alkylene, an optionally substituted cycloalkyl, an optionally substituted aryl, and an optionally substituted arylalkyl; and $R_{12}$ and $R_{13}$ are independently hydrogen, an optionally substituted alkyl, an optionally cycloalkyl, an optionally substituted heterocyclyl, an optionally substituted aryl, and an optionally substituted arylalkyl; or $R_2$ and $R_3$, $R_7$ and $R_8$, or $R_9$ and $R_{10}$ are linked together forming an optionally substituted ring selected from the group consisting of a five membered ring, a six membered ring, a seven membered ring, or an eight membered ring. In a more preferred embodiment, $R_2$, $R_3$, $R_4$, $R_5$, $R_6$, $R_7$, $R_8$, $R_9$, $R_{10}$, and $R_{11}$ are hydrogens.

In some embodiments, the compound has the chemical structure of formula I:

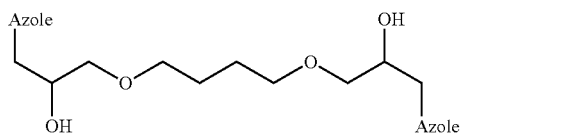

Formula I where the azole is selected from the group consisting of:

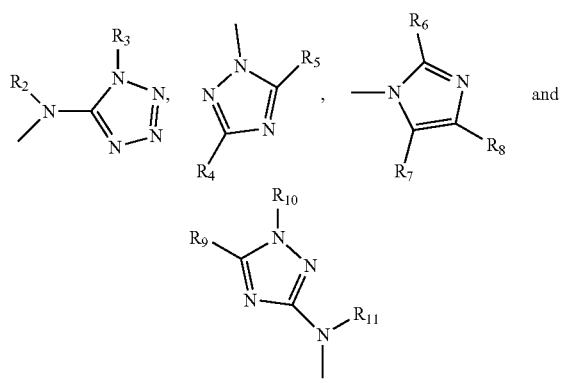

wherein $R_2$, $R_3$, $R_4$, $R_5$, $R_6$, $R_7$, $R_8$, $R_9$, $R_{10}$, and $R_{11}$ are independently selected from the group consisting of a hydrogen, $NR_{12}R_{13}$, $OR_{12}$, $SR_{12}$, $SeR_{12}$, an optionally substituted alkyl, an optionally substituted alkylene, an optionally substituted cycloalkyl, an optionally substituted aryl, and an optionally substituted arylalkyl; and $R_{12}$ and $R_{13}$ are independently hydrogen, an optionally substituted alkyl, an optionally cycloalkyl, an optionally substituted heterocyclyl, an optionally substituted aryl, and an optionally substituted arylalkyl; or $R_2$ and $R_3$, $R_7$ and $R_8$, or $R_9$ and $R_{10}$ are linked together forming an optionally substituted ring selected from the group consisting of a five membered ring, a six membered ring, a seven membered ring, or an eight membered ring.

In some preferred embodiment, $R_2$, $R_3$, $R_1$, $R_5$, $R_6$, $R_7$, $R_8$, $R_9$, $R_{10}$, $R_{11}$ are hydrogens.

The compounds of formula $A(BC)_n$ can obtained by organic synthesis by a coupling reaction of two compounds having the appropriate functional groups. At least one of the two compounds contains an azole moiety or a precursor functionality which can be converted to an azole moiety after the coupling reaction. The two compounds may be coupled through the formation of ether, thioether, amino, imino, amide, sulfoxide, sulfonamide, carbamate, or urea linkages by well-known methods in the art. The discussion below describes non-limiting examples of some of the methods of making exemplified linkages.

Williamson synthesis leads to the formation of an ether linkage by the reaction of alkyl halide and alkoxide ion. For example, the reaction of 1,4-butanediol with allyl bromide in the presence of sodium metal produces diallyl 1,4-butane ether. Alternatively, the reaction of 1,4-dibromobutane with allyl alcohol in the presence of sodium metal produces diallyl 1,4-butane ether. Epoxidation of diallyl 1,4-butane ether with m-chloroperbenzoic acid or hydrogen peroxide followed by the reaction of the epoxide with an azole produces a compound of formula $A(BC)_2$. As used herein, the term polyol refers to any organic compound having at least two hydroxyl groups. Polyols that may be used in the Williamson synthesis include, but are not limited to ethylene glycol, propylene glycol, glycerol, reduced sugars such as but not limited to sorbitol, isomers of cyclohexanediol, isomers of cyclopentanediol, oligomers or polymers of ethylene glycol, oligomers or polymer of ethylene or propylene glycol, and the like. Any primary or secondary alkyl halide is suitable for use in Williamson syntheses to produce an ether linkage as long as it contains an azole moiety or a functionality that allows the introduction of an azole moiety. Examples of suitable alkyl halide include but are not limited to allyl halide, α-haloacids such as but not limited to chloroacetic acid or bromopropionic acid, α-haloaldehyde or α-haloketones such as but not limited to chloroacetone, bromoacetaldehyde, and the like.

Another well-known method for the formation of ether linkages is the alkoxymercuration-demercuration method which involves the reaction of an alkene with an alcohol in the presence of mercuric trifluoroacetate followed by sodium borohydride reduction to produce ether. For example, the reaction of 1,3-butadiene with 1-hydroxyethylene-2-azole in the presence of mercuric trifluoroacetate followed by sodium borohydride reduction would produce a compound having the chemical formula:

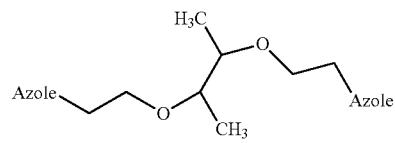

The formation of a thioether linkage may be accomplished by the reaction of thiols with alkyl halides or esters of sulfonic acid, known as tosyl alkyl esters, in the presence of a base such as alkali metal hydroxide or carbonate. Many thiols are commercially available such as, but not limited to mercaptoethanol, dithiothreitol, allyl mercaptan, 1,3-propanedithiol, 1,4-propanedithiol, 1,5-pentanedithiol, 1,6-hexanedithiol, and isomers thereof, and may be used to make the compounds of the invention.

Similarly, the reactions of amines with alkyl halide or tosyl alkyl esters produce an amine linkage between two molecules. Examples of the amine compounds include, but are not limited to ethylene diamine, 1,3-diaminopropane, 1,4-diaminopropane, diethylene triamine, 1,6-hexane diamine, and isomers thereof and the like.

The formation of amide bond also provides a linkage between two molecules. For example, carboxylic acids such as, but not limited to haloacetic acid, oxalic acid, malonic acid, succinic acid, glutaric acid, adipic acid, maleic acid, fumaric acid, phathalic acid, isothalic acid, terephthalic acid, and the like may be utilized to make the compound of the invention. Said carboxylic acids may be coupled with amines such as allyl amine, ethylene diamine, 1,3-diaminopropane, 1,4-diaminopropane, diethylene triamine, 1,6-hexane diamine, and isomer thereof and the like using a reactive derivative of the carboxylic acid such as, but not limited to reactive esters, acid anhydrides, and acid chlorides. Alternatively, a coupling reagent such as dicyclohexyldiimide, carbonyl diimidazole, and the like may be used to couple a carboxylic acid and an amine. The coupling of L- or D-histidine, imidazole containing amino acid, to a carboxylic acid or an amine using properly protected amino or carboxyl group produces compounds within the scope of the invention.

Similarly, the formation of sulfoxide, sulfonamide, carbamate, or urea linkages are well known in the art and may be utilized to make the compounds of the invention.

Azole-containing compounds can be produced by nucleophilic attachment of an azole ring nitrogen or O, S; or a ring substituent such as, but not limited to, amino group, hydroxyl group, and thiol group on alkyl halide, alkyl tosylate, or an epoxide ring to produce an azole compound.

A second aspect of the invention is directed to compositions, in particular a pharmaceutical composition wherein the active ingredient is at least one of the compounds of the invention.

As used herein, a "composition" or a "pharmaceutical composition" refers to a mixture of the active ingredient with other chemical components, such as pharmaceutically acceptable carriers and excipients. One purpose of a composition is to facilitate administration of one or more compound of the invention to a subject. Pharmaceutical compositions of the present disclosure may be manufactured by processes well-known in the art, e.g., by means of conventional mixing, dissolving, granulating, dragee-making, levigating, emulsifying, encapsulating, entrapping or lyophilizing processes. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The term "active ingredient", as used herein, refers to an ingredient in the composition that is biologically active, for example, at least one of the compounds of the invention, a salt thereof, a solvate thereof, a tautomer thereof, a stereoisomer thereof, or any mixtures thereof.

In one or more embodiments, the pharmaceutical composition comprises at least 0.01 wt %, 0.05 wt %, 0.1 wt %, 0.5 wt %, 5 wt %, 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, 95 wt %, 99 wt %, or 99.9 wt % of the compound of the invention relative to the total weight of the composition. The pharmaceutical composition may contain 0.1-400 μM, 1-300 μM, preferably 10-200 μM of at least one compound of the invention relative to the total volume of the composition. In some embodiments, the composition comprises up to 0.1 wt %, 1 wt %, 5 wt %, or 10 wt % of a pharmaceutically acceptable salt of at least one compound of the invention. In some embodiments, the composition comprises up to 0.1 wt %, 1 wt %, 5 wt %, or 10 wt % of a pharmaceutically acceptable solvate of at least one compound of the invention. Preferably, the composition may further comprise pharmaceutically acceptable binders, such as sucrose, lactose, xylitol, and pharmaceutically acceptable excipients such as calcium carbonate, calcium phosphate, and dimethyl sulfoxide (DMSO).

In some embodiments, the ability of the active ingredient to reduce the viability of cancer cells may be determined by contacting the pharmaceutical composition with the cancer cells and then performing cell viability assays. Methods of such assays include, without limitation, ATP test, Calcein AM assay, clonogenic assay, ethidium homodimer assay, Evans blue assay, fluorescein diacetate hydrolysis/Propidium iodide staining assay, flow cytometry, Formazan-based assays (MTT, XTT), green fluorescent protein assay, lactate dehydrogenase (LDH) assay, methyl violet assay, propidium iodide assay, Resazurin assay, trypan blue assay, and TUNEL assay. In a preferred embodiment, a MTT assay is used.

In some embodiments, the cancer cells are derived from human cancer cell lines, including, but not limited to, colon cancer cell lines, e.g., HCT15, MDST8, GP5d, HCT116, DLD1, HT29, SW620, SW403 and T84, lung cancer cell lines, e.g., A549, SHP-77, COR-L23/R, and NCI-H69/LX20, breast cancer cell lines, e.g., MDA-MB-231, MCF7, T47D, and VP303, cervical cancer cell Lines, e.g., HeLa DH, HtTA-1, HRS, and C-4I, ovarian cancer cell lines, e.g., A2780, A2780cis, OV7, and PEO23, and skin cancer cell lines, e.g., C32TG, A375, and MCC26. In other embodiments, the cancer cells are collected from a human patient who is at risk of having, is suspected of having, has been diagnosed with, or is being monitored for recurrence of at least one type of cancer, preferably colon cancer, lung cancer, cervical cancer, testicular cancer, and/or breast cancer.

As used herein, the terms "sufficient amount" or "cytotoxic effective amount" are used interchangeably, and are intended to refer to a concentration of the active ingredient that reduces the viability of the cancer cells by at least 5%, 10%, 15%, 20%, 30%, 40%, 50%, 60%, 70%, 80% or 90%, relative to cancer cells not treated with the active ingredient. The reduction in viability may occur no more than 10 days, 7 days, 5 days, 3 days, or 2 days after the active ingredient is contacted with the cancer cells. In one embodiment, the cytotoxic effective amount may be the $IC_{50}$ which is a concentration of the active ingredient which causes the death of 50% of cancer cells in 72 hours (3 days). In one embodiment, the $IC_{50}$ of at least one compound of the invention, the salt thereof, the solvate thereof, the tautomer thereof, the stereoisomer thereof, or the mixture thereof against colon cancer cells is in a range of 0.01-150 μM, preferably 1-70 μM, more preferably 30-40 μM. In another embodiment, the $IC_{50}$ of at least one compound of the invention, the salt thereof, the solvate thereof, the tautomer thereof, the stereoisomer thereof; or the mixture thereof against lung cancer cells is in a range of 0.01-200 μM, preferably 1-80 μM, more preferably 40-50 μM. In another embodiment, the $IC_{50}$ of at least one compound of the invention, the salt thereof, the solvate thereof, the tautomer thereof, the stereoisomer thereof, or the mixture thereof against breast cancer cells is in a range of 0.01-120 μM, preferably 1-60 μM, more preferably 40-50 μM.

In some embodiments, other active ingredients in addition to one or more of the azole compound of the current disclosure may be incorporated into a pharmaceutical composition. In one embodiment, the pharmaceutical composition includes a second active ingredient, such as a chemotherapeutic agent or an anticancer agent, for the treatment or prevention of neoplasm, tumor or cancer cell division, growth, proliferation and/or metastasis in the subject; induction of death or apoptosis of tumor and/or cancer cells; and/or any other forms of proliferative disorder.

As used herein, other non-cancerous proliferative disorders that may also be treated by the currently disclosed pharmaceutical composition include, without limitation, atherosclerosis, rheumatoid arthritis, psoriasis, idiopathic pulmonary fibrosis, scleroderma, cirrhosis of the liver, lymphoproliferative disorder, other disorders characterized by epidermal cell proliferation such as verruca (warts), and dermatitis, and benign proliferative breast disease such as ductal hyperplasia, lobular hyperplasia, and papillomas.

The anticancer agent is at least one of a mitotic inhibitor; an alkylating agent; an antimetabolite; a cell cycle inhibitor; an enzyme; a topoisomerase inhibitor; a biological response modifier; an anti-hormone; an antiangiogenic agent such as MMP-2, MMP-9 and COX-2 inhibitor; an anti-androgen; a platinum coordination complex such as, but not limited to cisplatin, oxaliplatin, carboplatin; a substituted urea such as hydroxyurea; a methylhydrazine derivative; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane).

Exemplary anticancer agents include, but are not limited to, alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; anti-microtubule agents including etoposide, vinblastine, vincristine, teniposide, docetaxel, paclitaxel, vinorelbine, vindesine; cytotoxic antibiotics including daunorubicin, doxorubicin, idarubicin, mitomycin, actinomycin, epirubicin; topoisomerase inhibitors including irinotecan, mitoxantrone, topotecan, and mixtures thereof.

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include antioxidants including ascorbic acid; low molecular weight (less than about 10 residues) polypeptides; proteins, such as serum albumin, gelatine, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrin; chelating agents such as EDTA; sugar alcohols such as mannitol or sorbitol; salt-forming counter ions such as sodium; and/or non-ionic surfactants such as TWEEN® (ICI, inc.; Bridgewater, N.J.), polyethylene glycol (PEG), and PLURONICS® (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatine, vegetable oils, and polyethylene glycols.

In some embodiments, the pharmaceutically acceptable carrier and/or excipient is at least one selected from the group consisting of a buffer, an inorganic salt, a fatty acid, a vegetable oil, a synthetic fatty ester, a surfactant, and a polymer.

Exemplary buffers include, without limitation, phosphate buffers, citrate buffer, acetate buffers, borate buffers, carbonate buffers, bicarbonate buffers, and buffers with other organic acids and salts.

Exemplary inorganic salts include, without limitation, calcium carbonate, calcium phosphate, disodium hydrogen phosphate, potassium hydrogen phosphate, sodium chloride, zinc oxide, zinc sulfate, and magnesium trisilicate.

Exemplary fatty acids include, without limitation, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, without limitation, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to an monoether or diester, or mixtures thereof formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidycholine, and 3-[(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethylammonium bromide, tetradecyltrimethylammonium bromide, tetradecyltrimethyl-ammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Depending on the route of administration e.g. oral, parental, or topical, the composition may be in the form of solid dosage form such as tablets, caplets, capsules, powders, and granules, semi-solid dosage form such as ointments, creams, lotions, gels, pastes, and suppositories, liquid dosage forms such as solutions, and dispersions, inhalation dosage form such as aerosols, and spray, or transdermal dosage form such as patches.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatine, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavouring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, find use in the preparation of injectable. Dimethyl acetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration may involve the use of transdermal administration such as transdermal patches or iontophoresis devices. Formulation of drugs is discussed in, for example, Hoover, J. E. Remington's pharmaceutical sciences, Mack Publishing Co., Easton, Pa., 1975; and Liberman, H. A.; Lachman, L., Eds. Pharmaceutical dosage forms, Marcel Decker, New York, N.Y., 1980, which are incorporated herein by reference in their entirety.

In other embodiments, the composition having an azole compound disclosed herein, the salt thereof, the solvate thereof, the tautomer thereof, the stereoisomer thereof, or the mixture thereof has different release rates categorized as immediate release and controlled- or sustained-release.

As used herein, immediate release refers to the release of an active ingredient substantially immediately upon administration. In another embodiment, immediate release occurs when there is dissolution of an active ingredient within 1-20 minutes after administration. Dissolution can be of all or less than all (e.g. about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release, or sustained-release, refers to a release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. In one embodiment, the composition is not a controlled-release composition.

According to a third aspect, the current disclosure relates to a method for treating a proliferative disorder, comprising administering to a subject in need of therapy a sufficient amount of a pharmaceutical composition comprising a compound having the chemical formula $A(BC)_n$, or a salt thereof, a solvate, a tautomer thereof, a stereoisomer thereof, or a mixture thereof, wherein:

A is optionally substituted linear or branched carbon chain having 2 to 12 carbon atoms, an optionally substituted carbocyclic ring having 4 to 6 carbon atoms, an optionally substituted aromatic ring, optionally substituted biphenyl, or HO—(CHR$_1$CH$_2$O)$_x$H, wherein R$_1$ is hydrogen, methyl or ethyl and x is an integer in the range of 2 to 10, B is a linking functionality selected from the group consisting of ether, thioether, amino, amido, sulfonamide, carbamate, and urea, C is an azole containing moiety, and n is an integer in the range of 1 to 6.

In another preferred embodiment of the method, the azole is selected from the group consisting of:

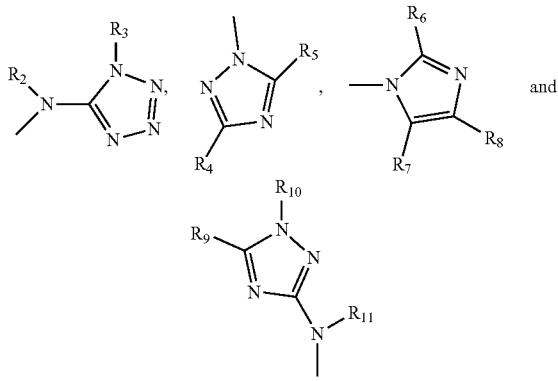

wherein R$_2$, R$_3$, R$_4$, R$_5$, R$_6$, R$_7$, R$_8$, R$_9$, R$_{10}$, and R$_{11}$ are independently selected from the group consisting of a hydrogen, NR$_{12}$R$_{13}$, OR$_{12}$, SR$_{12}$, SeR$_{12}$, an optionally substituted alkyl, an optionally substituted alkylene, an optionally substituted cycloalkyl, an optionally substituted aryl, and an optionally substituted arylalkyl; and R$_{12}$ and R$_{13}$ are independently hydrogen, an optionally substituted alkyl, an optionally cycloalkyl, an optionally substituted heterocyclyl, an optionally substituted aryl, and an optionally substituted arylalkyl; or R$_2$ and R$_3$, R$_7$ and R$_8$, or R$_9$ and R$_{10}$ are linked together forming an optionally substituted ring selected from the group consisting of a five membered ring, a six membered ring, a seven membered ring, or an eight membered ring.

As used herein, the terms "treat", "treatment", and "treating" in the context of the administration of a therapy to a subject in need thereof refer to the reduction or inhibition of the progression and/or duration of a disease (e.g. cancer), the reduction or amelioration of the severity of the disease, and/or the amelioration of one or more symptoms thereof resulting from the administration of one or more therapies. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such terms may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumour size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

The term "subject" and "patient" are used interchangeably. As used herein, they refer to any subject for whom or which therapy, including with the compositions according to the present disclosure is desired. In most embodiments, the subject is a mammal, including but is not limited to a human, a non-human primate such as a chimpanzee, a domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human.

In one or more embodiments, the proliferative disorder is cancer. In some embodiments, the disclosed method of the fourth aspect is for treating cancer of the blood, brain, bladder, lung, cervix, ovary, colon, rectum, pancreas, skin, prostate gland, stomach, breast, spleen, liver, kidney, head, neck, testicle, bone, bone marrow, thyroid gland, or central nervous system. In a preferred embodiment, the cancer is at least one selected from the group consisting of colon cancer, cervical cancer, breast cancer, and lung cancer. In a more preferred embodiment, the cancer is cervical cancer or breast cancer. In the most preferred embodiment, the cancer is cervical cancer or breast cancer.

As used herein, a subject in need of therapy includes a subject already with the disease, a subject which does not yet experience or exhibit symptoms of the disease, and a subject predisposed to the disease. In preferred embodiments, the subject is a person who is predisposed to cancer, e.g. a person with a family history of cancer. People who (i) had inflammatory bowel disease, or a genetic syndrome such as familial adenomatous polyposis (FAP) and hereditary non-polyposis colorectal cancer (Lynch syndrome), and/or (ii) consumes a low-fiber and high-fat diet are at a higher risk of contracting colon cancer. White women or a person with (i) certain inherited genes (e.g. mutated BRCA1, BRCA2, ATM, TP53, CHEK2, PTEN, CDH1, STK11, and PALB2), (ii) radiation occurred to one's chest, and/or (iii) exposure to diethylstilbestrol (DES) are at a higher risk of contracting breast cancer. People who (i) smoke or regularly breathe in second-hand smoke, (ii) exposed to carcinogens including, but not limited to polycyclic aromatic hydrocarbons (e. g. benzo[a]pyrene, benz[a]anthracene, and methylated derivatives thereof), asbestos, radioactive substances (e.g., uranium, radon), and/or (iii) inhaled chemicals or minerals (e.g., arsenic, beryllium, cadmium, silica, vinyl chloride, nickel compounds, chromium compounds, coal products, mustard gas, and chloromethyl ethers) are at a higher risk of contracting lung cancer.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral mutes, intraduodenal mutes, parenteral injection (including intravenous, subcutaneous, intraperitoneal, intramuscular, intravascular, or infusion), topical and rectal administration. Those of ordinary skill in the art are familiar with administration techniques that can be employed with the compounds and methods described herein. In preferred embodiments, the active ingredient and/or the composition described herein are administered orally.

In one or more embodiments, the pharmaceutical composition administered comprises one or more compounds of the invention, or a salt thereof, a solvate thereof, a tautomer thereof, a stereoisomer thereof or a mixture thereof.

The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount", "therapeutically effective amount", "pharmaceutically effective amount" or sufficient amount refer to that amount of the active ingredient being administered which will relieve to some extent one or more of the symptoms of the disease being treated. The result can be a reduction and/or alleviation of the signs, symptoms, or causes of a disease, or any other desired alteration of a biological system. An appropriate "effective amount" may differ from one individual to another. An appropriate "effective amount" in any individual case may be determined using techniques, such as a dose escalation study. In some embodiments, an effective amount of the compound of the invention is in a range of 1-300 mg/kg, preferably 10-200 mg/kg, more preferably 50-100 mg/kg is administered per body weight of the subject.

In treating certain cancers, the best approach is often a combination of surgery, radiotherapy, and/or chemotherapy. Therefore, in at least one embodiment, the pharmaceutical composition is employed in conjunction with radiotherapy. In another embodiment, the pharmaceutical composition is employed with surgery. The radiotherapy and/or surgery may be before or after the composition is administered.

A treatment method may comprise administering a pharmaceutical composition containing one or more compound of the current disclosure as a single dose or multiple individual divided doses. In some embodiments, the composition is administered at various dosages (e.g. a first dose with an effective amount of 200 mg/kg and a second dose with an effective amount of 50 mg/kg). In some embodiments, the interval of time between the administration of the composition and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, 5 days, 6 days, or 7 days. In certain embodiments, the composition and one or more additional therapies are administered less than 1 day, 1 week, 2 weeks, 3 weeks, 4 weeks, 1 month, 2 months, 3 months, 6 months, 1 year, 2 years, or 5 years apart.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, 10%, 15%, 20%, 25%, 30%, 40%, 50%, 60%, 70%, 75%, 80%, 85%, 90%, 95%, 99%, or 100%, relative to the tumor size before treatment. In other embodiments, the size of a tumor after treatment does not reduce but is maintained the same as the tumor size before treatment. Methods of assessing tumor size include, but are not limited to, CT scan, MRI, DCE-MRI and PET scan.

In most embodiments, the method further comprises measuring a concentration of a biomarker and/or detecting a mutation in a biomarker before and/or after the pharmaceutical composition comprising comprises one or more compounds of the present disclosure is administered. As used herein, the term "biomarker" refers to a characteristic that is objectively measured and evaluated as an indicator of normal biological processes, pathogenic processes or pharmacological responses to a therapeutic intervention. Generic cancer biomarkers include circulating tumor DNA (ctDNA) and circulating tumor cells (CTC). Exemplary biomarkers for colon cancer include, without limitation, carcinoembryonic antigen (CEA), carbohydrate antigen 242 (CA 242), CA 195, CA 19-9, MSI, and 18qLOH. Exemplary biomarkers for breast cancer include, without limitation, BRCA1, BRCA2, HER-2, estrogen receptor, progesterone receptor, CA 15-3, CA 27.29, CEA, Ki67, cyclin D1, cyclin E, and ERβ. Exemplary biomarkers for lung cancer include, without limitation, CA 125, CA 15-3, EGF receptor, anaplastic lymphoma kinase gene, MET, ROS-1, and KRAS. Potentially predictive cancer biomarkers include, without limitation, mutations in genes BRCA1 and BRCA2 for breast cancer and/or ovarian cancer, overexpression of CEA, NSE, CYFRA-21-1, CA-125, and CA-199 for lung cancer, overexpression of TYMS, mutations in genes p53 and KRAS for colon cancer.

The mutation in the biomarker may be detected by procedures such as restriction fragment length polymorphism (RFLP), polymerase chain reaction (PCR) assay, multiplex ligation-dependent probe amplification (MLPA), denaturing gradient gel electrophoresis (DGGE), single-strand conformation polymorphism (SSCP), hetero-duplex analysis, protein truncation test (PTT), and oligonucleotide ligation assay (OLA). The procedures to detect the mutation are well-known to those of ordinary skill in the art.

The term "sample" used herein refers to any biological sample obtained from the subject in need of therapy including a single cell, multiple cells, fragments of cells, a tissue sample, and/or body fluid. Specifically, the biological sample may include red blood cells, white blood cells, platelets, hepatocytes, epithelial cells, endothelial cells, a skin biopsy, a mucosa biopsy, an aliquot of urine, saliva, whole blood, serum, plasma, lymph. In some embodiments, the biological sample is taken from a tumor.

The concentration level of the cancer biomarker in a sample may be measured by an assay, for example an immunoassay. Typical immunoassay methods include, without limitation, enzyme-linked immunosorbent assay (ELISA), enzyme-linked immunospot assay (ELISPOT), Western blotting, immunohistochemistry (IBC), immunocytochemistry, immunostaining, and multiple reaction monitoring (MRM) based mass spectrometric immunoassay. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

In some embodiments, the concentration of the biomarker is measured before and after the administration. When the concentration of the biomarker is maintained, the method may further comprise increasing the effective amount of the azole compound of the invention by at least 5%, at least 10%, or at least 30%, up to 50%, up to 60%, or up to 80% of an initial effective amount that is in a range of 1-300 mg/kg per body weight of the subject. The increased effective amount may be in a range of 1.05-540 mg/kg, preferably 15-420 mg/kg, more preferably 25-270 mg/kg. The subject may be administered with the increased dosage for a longer period (e.g. 1 week more, 2 weeks more, or 2 months more) than the duration prescribed with the initial effective amount.

In some embodiments, the mutation in the biomarker is detected before administering the composition to identify subjects predisposed to the disease. For example, subjects with a BRCA1 germline mutation are at a higher risk of contracting breast cancer, or ovarian cancer. In some embodiments, the biomarkers are measured/detected after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

In some embodiments, the administration is stopped once the subject is treated.

Having generally described this disclosure, a further understanding can be obtained by reference to certain specific examples which are provided herein for purposes of illustration only and are not intended to be limiting unless otherwise specified.

Example 1

Synthesis and Characterization of Azole and its Derivatives
Materials: Imidazole (Imi)≥99% (AK Scientific Inc.), 1,2,4-Triazole (Tri) (AK Scientific Inc), 3-Amino-1H-1,2,4-Triazole (ATri) (AK Scientific Inc), 1,4-Butanediol diglycidyl ether 295% (BG) Phosphoric acid (H3PO4) puriss, ≥299% (AK Scientific Inc), 5-Aminotetrazole Monohydrate (ATet) 97% (Sigma Aldrich Company), and dimethyl sulfoxide (DMSO) (Merck).

Figure 1B:
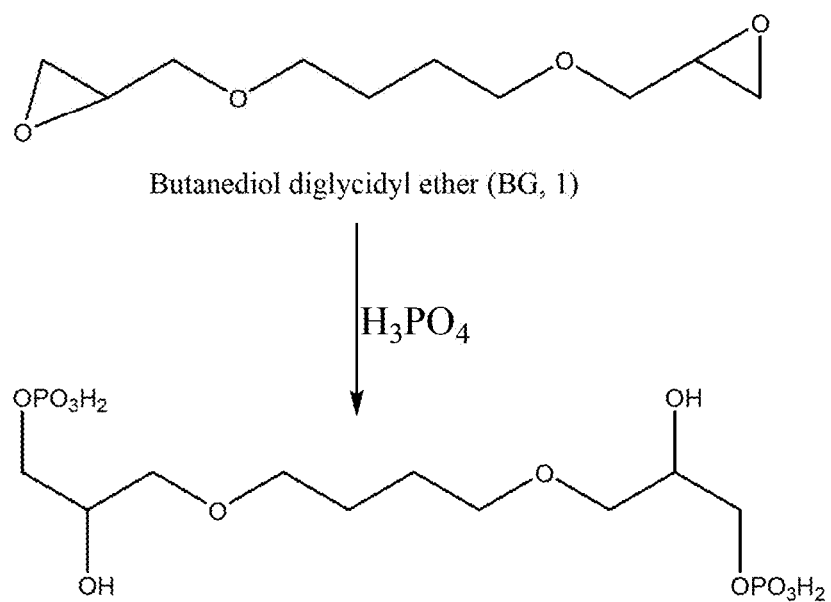
FIG. 1B shows the chemical structure of 1,4-butanediol diglycidyl ether (BG, 1) and phosphoric acid conjugate of BG, compound 6.

Azoles terminated 1,4-butanediol diglycidyl ether (BG) were prepared by the reaction of different azoles via epoxide ring opening. In a typical synthesis, 0.68 g (10 mmol) imidazole was added to a solution of 1.0 g (5 mmol) of 1,4-butanediol diglycidyl ether in DMSO. The reaction mixture was heated to 80° C. and continuously stirred for 4 hours. The solvent was evaporated under vacuum overnight. The final material was washed with dialyzed to get rid of any unreacted materials. All other azoles, i.e., 1,2,4-Triazole, 3-Amino-1H-1,2,4-triazole, 5-aminotetrazole and phosphoric acid were reacted with BG in a similar procedure, see FIGS. 1A and 1B.

FT-IR Analysis:

Fourier-transform infrared (FTIR) spectrophotometer Spectrum (PerkinElmer, USA) was employed to record FTIR spectra of samples in the range of 400-4000 cm$^{-1}$ with a resolution of 4 cm$^{-1}$ at room temperature. The differences in spectral peaks of the BG-(Tri)$_2$, BG-(ATri)$_2$, BG-(Atet)$_2$, BG-(Imi)$_2$, BG-(H$_3$PO$_4$)$_2$ were then evaluated.

Figure 2:
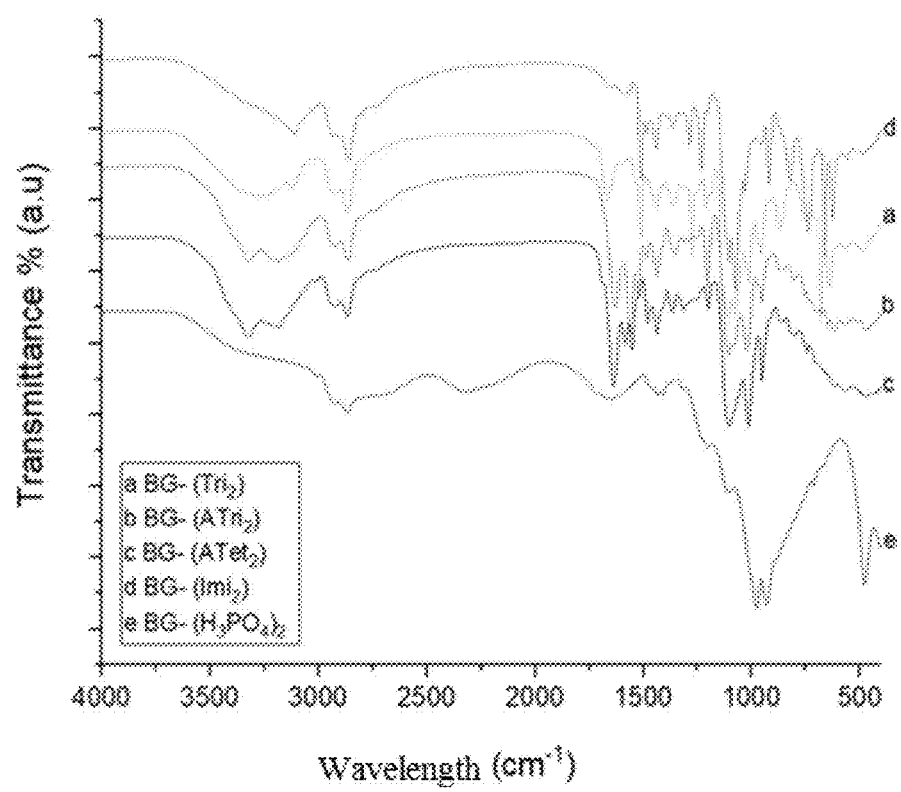
FIG. 2 shows FT-IR spectra of (a) BG-(Tri$_2$), compound 3; (b) BG-(ATri2) compound 4; (c) BG-(ATet$_2$), compound 5; (d) BG-(Imi$_2$) compound 2, and (e) BG-(H$_3$PO$_4$)$_2$, compound 6.
Figure 3:
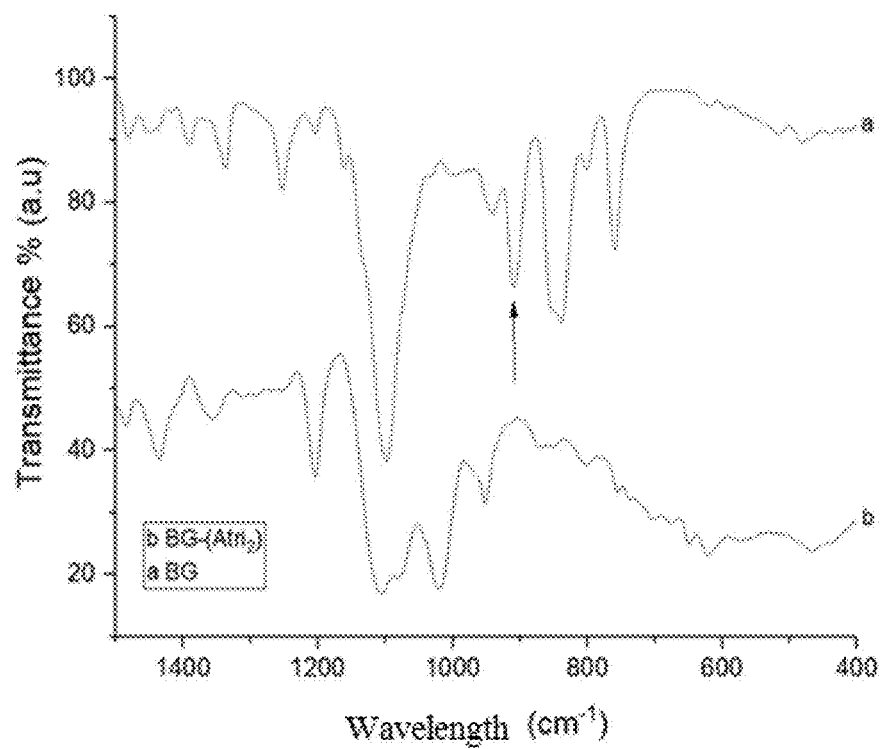
FIG. 3 shows FT-IR spectra of (a) BG-(Tri$_2$), and (b) BG. The difference in the FT-IR spectra between BG and BG-(ATri$_2$) is shown with the arrow.

FIG. 2 shows FT-IR spectra of (a) BG-(Tri)$_2$, (b) BG-(ATri)$_2$, (c) BG-(Atet)$_2$, (d) BG-(Imi)$_2$, (e) BG-(H$_3$PO$_4$)$_2$. The strong absorption peaks at 1140 and 1260 cm$^{-1}$ was assigned to ester group that is C—O stretching [Çelik et al. (2008) "Proton-Conducting Properties of Acid-Doped Poly (glycidyl methacrylate)-1,2,4-Triazole Systems" Macromolecular Chemistry and Physics, 209: 593-603]. The —CH$_2$— stretching peaks belonging to —CH$_2$CH$_2$O— units 2866 cm$^{-1}$ peak. The stretching of the epoxy group which occurred near 910 cm$^{-1}$, disappeared upon the addition of azole (FIG. 3). BG-Tri exhibited characteristic medium absorption peak at 1502 and 1420 cm$^{-1}$ due to ring C—N stretching of the triazole. Additionally, the peak at 1663 cm$^{-1}$ belong to —N=N— stretching. Vibration peak for —N=N— stretching was previously reported at 1666 cm-1 [Trivedi and Tallapragada (2015) 2015. "Characterization of Physical, Spectral and Thermal Properties of Biofield Treated 1,2,4-Triazole" Journal of Molecular Pharmaceutics & Organic Process Research, 03]. BG-(ATri)$_2$ showed peaks at 1431, 1535 cm$^{-1}$ and 1634 cm$^{-1}$ belong to azolic ring. Azole groups illustrated typical absorption peaks at 3115 cm$^{-1}$ due to aromatic C—H vibrations. The vibrational peak at 3287 cm$^1$ can be attributed to water coordinated with the azole ring. For phosphate ester terminated BG, two strong peaks which are PO$_2$ bending vibration and P—O symmetric stretching are located near 500 and 1000 cm$^{-1}$, respectively [Bouchet and Siebert (1999) "Proton conduction in acid doped polybenzimidazole" Solid State Ionics, 118: 287-99]. The broadening between 3000-1500 cm$^{-1}$ is due to hydrogen bonding network among the phosphate groups.

Figure 4A:
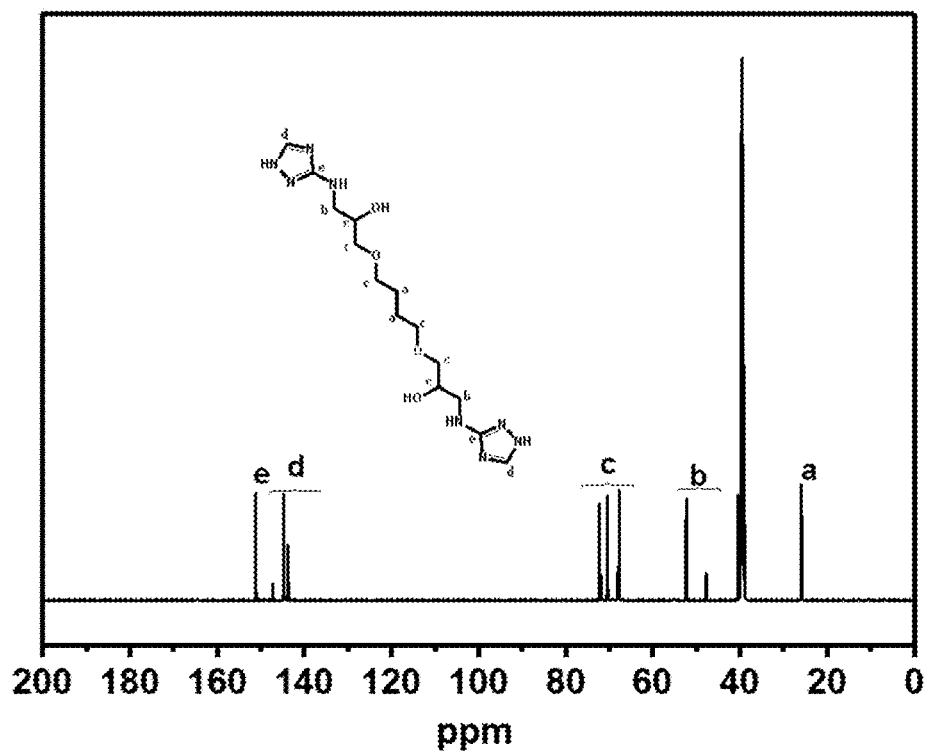
FIG. 4A shows $^{13}$C NMR spectrum for BG-(Atri$_2$).
Figure 4B:
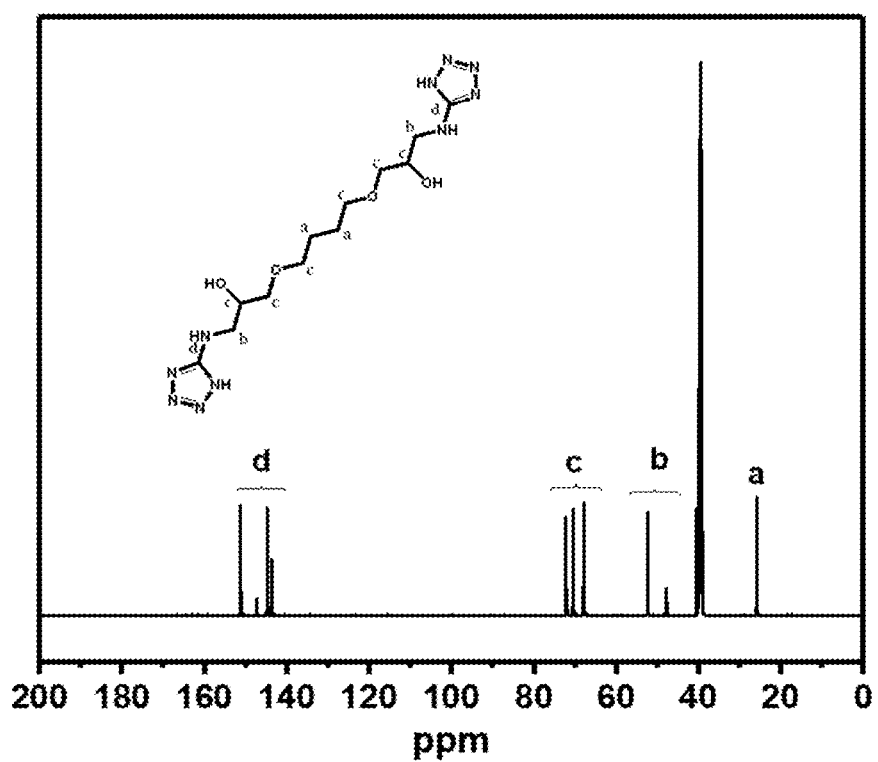
FIG. 4B shows $^{13}$C NMR spectrum for BG-(Atet$_2$).

$^{13}$C NMR:

FIGS. 4A and 4B show typical $^{13}$C NMR spectrum in DMSO-d$_6$ for BG-(Atri$_2$) and BG-(ATet$_2$), respectively. They exhibited similar carbon resonances between 20-80 ppm for the aliphatic carbons and the aromatic carbon resonance between 140-160 ppm region The spectral difference in this region may originate from the reaction procedure where the N—H sites of the ring may give additional reaction products [Çelik et al. (2008) "Proton-Conducting Properties of Acid-Doped Poly (glycidyl methacrylate)-1,2, 4-Triazole Systems" Macromolecular Chemistry and Physics, 209: 593-603

Thermogravimetric Analyses (TGA):

TGA were carried on Perkin-Elmer, simultaneous thermal analyzer (STA6000, PerkinElmer, Ohio, USA). TGA data of azole-BG samples were obtained at temperature in the range of 25° C. to 700° C. at the rate of 10° C. min under inert nitrogen flowing at a rate of 20 mL/min.

Figure 5:
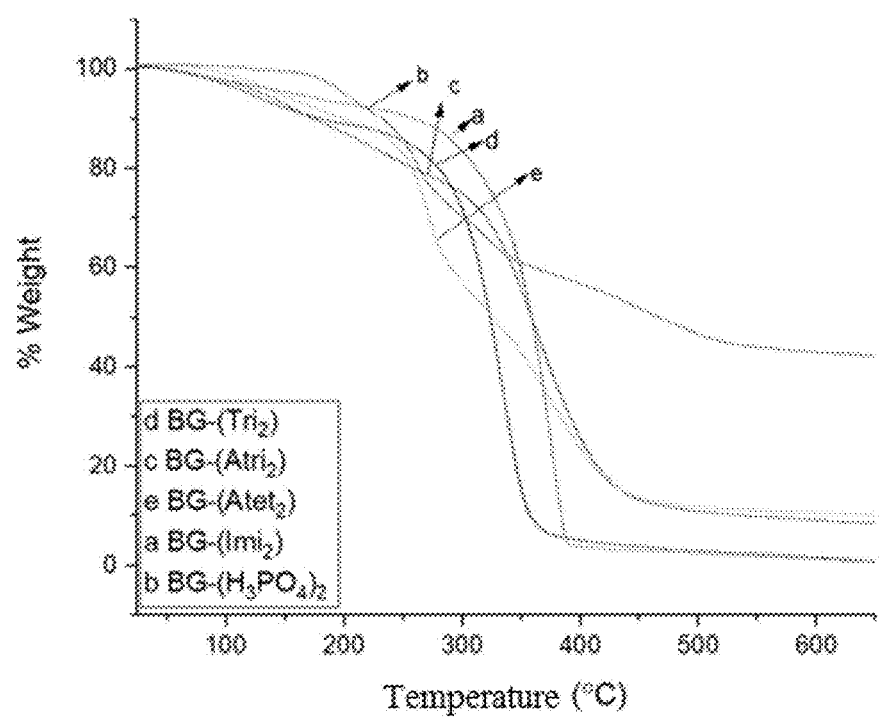
FIG. 5 show the TGA curves of TG of (a) BG-(Imi$_2$), (b) BG-(H$_3$PO$_4$)$_2$, (c) BG-(ATri$_2$), (d) BG-(Tri$_2$), and (e) BG-(ATet$_2$)

TGA analysis showed that the weight loss in Azole terminated BG occurred in several steps within 200-500° C. FIG. 5 shows the thermograms for (BG-(Tri)$_2$, BG-(ATri)$_2$, BG-(Atet)$_2$, BG-(Imi)$_2$, BG-(H$_3$PO$_4$)$_2$. For BG-(H$_3$PO$_4$)$_2$, there was no weight change for up to around 200° C. Above 200° C., the degradation of the BG-(H$_3$PO$_4$)$_2$ occurred in two step process. For azole terminated BG samples, a slight weight change between 100 to 200° C., could be attributed to loss of absorbed solvent. Above 250° C., the degradation of both BG-(Tri)$_2$ and BG-(Imi)$_2$ occurred in one step, but for other samples the decomposition occurred at several steps which may be due to degradation of azoles and ethoxy units. From TGA results, it is clearly demonstrated that all the azole and phosphonic acid terminated BGs have significant thermal stability for bio applications.

Example 2

Treatment of Cancer Cells with BG-Azole:

HCT-116 cells were grown as previously described method by Khan et al. ["Fluorescent magnetic submicronic polymer (FMSP) nanoparticles induce cell death in human colorectal carcinoma cells" Artif Cells Nanomed Biotechnol. (2018 Jul. 25) 1-7, doi: 10.1080/21691401.2018.1491476]. In brief, HCT-116 cells were grown in the DMEM, 10% fetal bovine serum, L-glutamine, selenium chloride, penicillin, and streptomycin. The cells were culture in incubator (Heracell 150i, Thermo-scientific, USA) containing 5% $CO_2$ at 37°. Finally, confluence cells were seeded into 96-well cell plates and once the cells become 80% confluence, the cancer cells were treated with different concentrations (100 μg/mL, 500 μg/mL and 750 μg/mL) of BG-(Tri)$_2$, BG-(ATri)$_2$, BG-(Atet)$_2$, BG-(Imi)$_2$, BG-($H_3PO_4$)$_2$, respectively. Thereafter, the treated cancer cells were microscopically monitored after 24 hrs and 48 hrs intervals. Three samples were examined from each experiment.

Cancer Cell Morphology:

After the treatments of cancer cells with BG-(Tri)$_2$, BG-(ATri)$_2$, BG-(Atet)$_2$, BG-(Imi)$_2$, and BG-($H_3PO_4$)$_2$, the cells were observed using inverted microscope (TS100F Eclipse, Nikon, Japan) to evaluate the anatomical and morphological changes and each sample was observed at 200 and 400 magnifications.

Cancer Cells Viability by MTT Assay:

The effects of BG-(Tri)$_2$, BG-(ATri)$_2$, BG-(Atet)$_2$, BG-(Imi)$_2$, BG-($H_3PO_4$)$_2$ on cancer cells were determined by MTT assay. The cancer cells were seeded with 6×10$^4$ cells/mL in 96-well culture plates containing DMEM, 10% Fetal bovine serum, penicillin, and streptomycin and were incubated in $CO_2$ incubator till they become 80% confluence. Then, cancer cells were treated with BG-(Tri)$_2$, BG-(ATri)$_2$, BG-(Atet)$_2$, BG-(Imi)$_2$, BG-($H_3PO_4$)$_2$ at concentrations of 100 μg/mL, 500 μg/mL and 750 μg/mL, respectively. The control experiments did not contain any of BG-(Tri)$_2$, BG-(ATri)$_2$, BG-(Atet)$_2$, BG-(Imi)$_2$, BG-($H_3PO_4$)$_2$. MTT (5.0 mg/mL) solution was added in each well and cells were again incubated for 4 hrs in the $CO_2$ incubator and finally media was changed with the addition of DMSO. The color intensity of each sample was measured using an ELISA plate reader (Biotek Instruments, USA) at wavelength 570 nm.

The following formula was used to calculate percentage of cell viability:

% of Cell viability=Optical density (O.D) of BG-(Tri)$_2$,BG-(ATri)$_2$,BG-(Atet)$_2$,BG-(Imi)$_2$,BG-($H_3PO_4$)$_2$ cells/Optical density (O.D) of control cells×100

Statistical Analysis:

The mean±standard deviation (SD) from control and BG-(Tri)$_2$, BG-(ATri)$_2$, BG-(Atet)$_2$, BG-(Imi)$_2$, BG-($H_3PO_4$)$_2$ treated groups were calculated. All statistical analyses were completed with GraphPad Prism 6 (GraphPad Software). The difference between control and BG-(Tri)$_2$, BG-(ATri)$_2$, BG-(Atet)$_2$, BG-(Imi)$_2$, BG-($H_3PO_4$)$_2$ groups by a one-way ANOVA test (P<0.05). P<0.05 was considered as statistically significant.

Figure 6A:
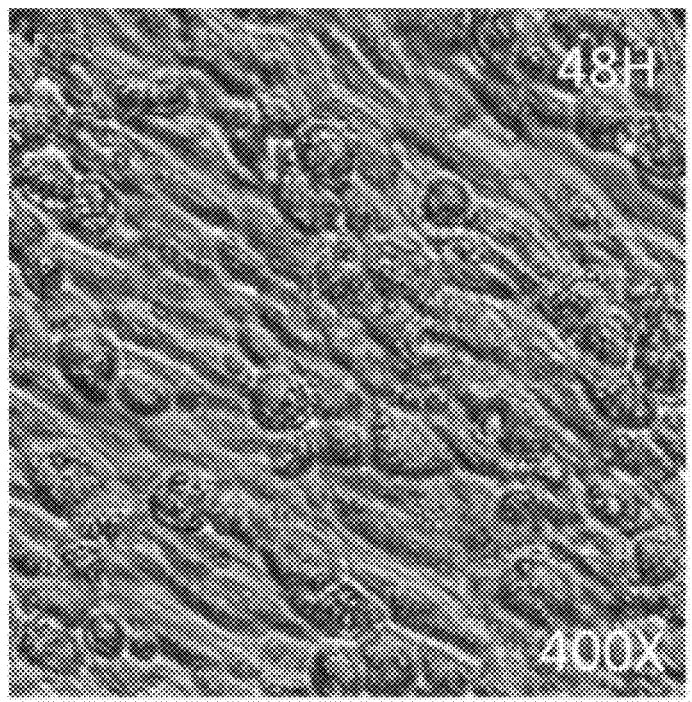
FIG. 6A shows cancer cells morphology of control HCT-116 cells.
Figure 6B:
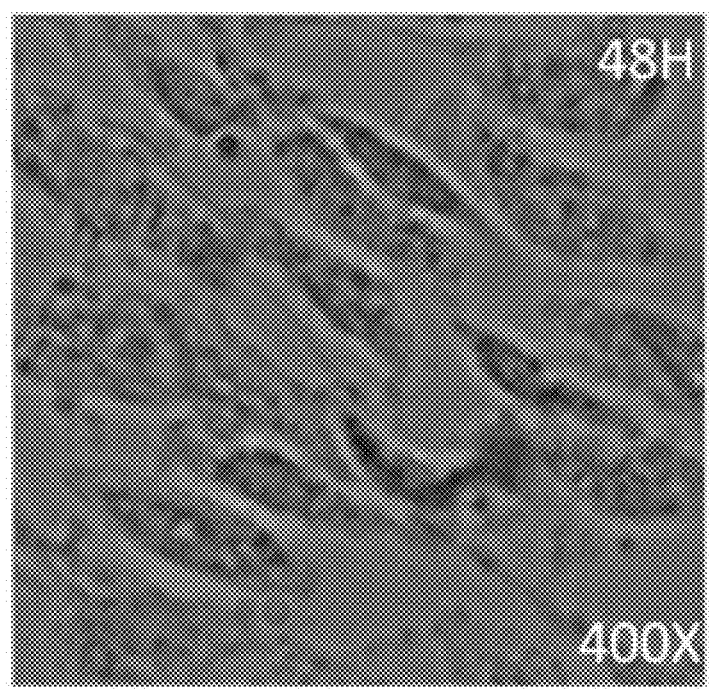
FIG. 6B shows cancer cells morphology of HCT-116 after 48 hours of treating the cells with 100 μg/mL of BG-(Tri)$_2$.
Figure 6C:
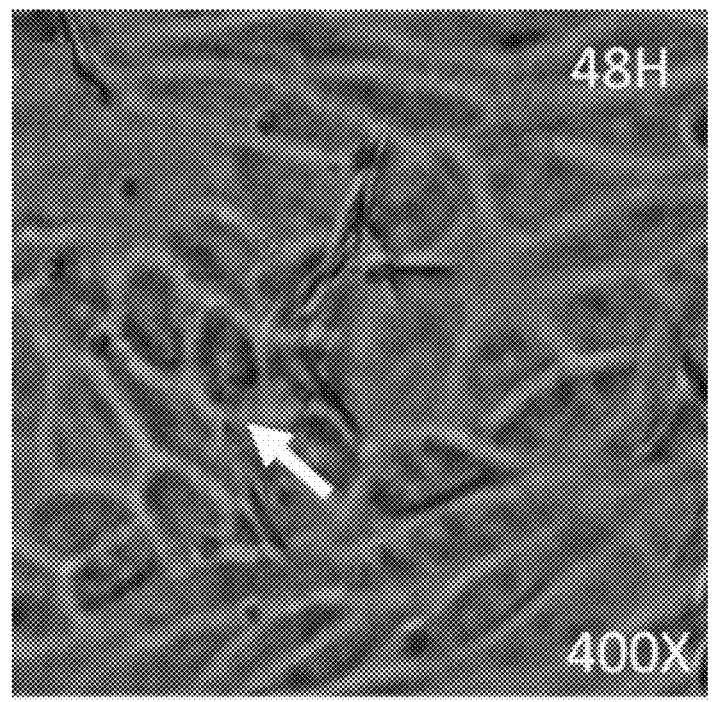
FIG. 6C shows cancer cells morphology of HCT-116 after 48 hours of treating the cells with 500 μg/mL of BG-(Tri)$_2$. The arrow points to a cancer cell nuclear condensation and augmentation at 400× magnifications.
Figure 6D:
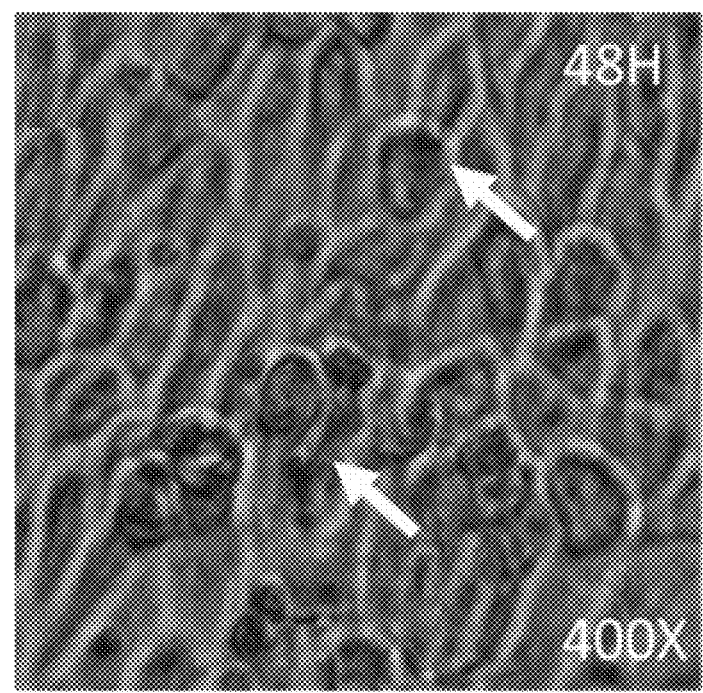
FIG. 6D shows cancer cells morphology of HCT-116 after 48 hours of treating the cells with 750 μg/mL of BG-(Tri)$_2$. The arrow points to a cancer cell nuclear condensation and augmentation at 400× magnifications.

Effect of BG-(Tri)$_2$ on Cancer Cell Morphology:

Post 48-hour treatment of cells with 100 μg/mL BG-(Tri)$_2$ resulted in moderate levels of nucleus condensation and nuclear augmentation of the HCT-116 cells (FIG. 6B) compared to control cells (FIG. 6A). Strong nuclear condensation and augmentation and the beginning of cell membrane disruption (FIG. 6C) was observed after 48 hours of treating the cells with 500 μg/mL showed. Treatment of the cells with 750 μg/mL led to a significant loss of cell population after 48 hours (FIG. 6D).

Figure 7A:
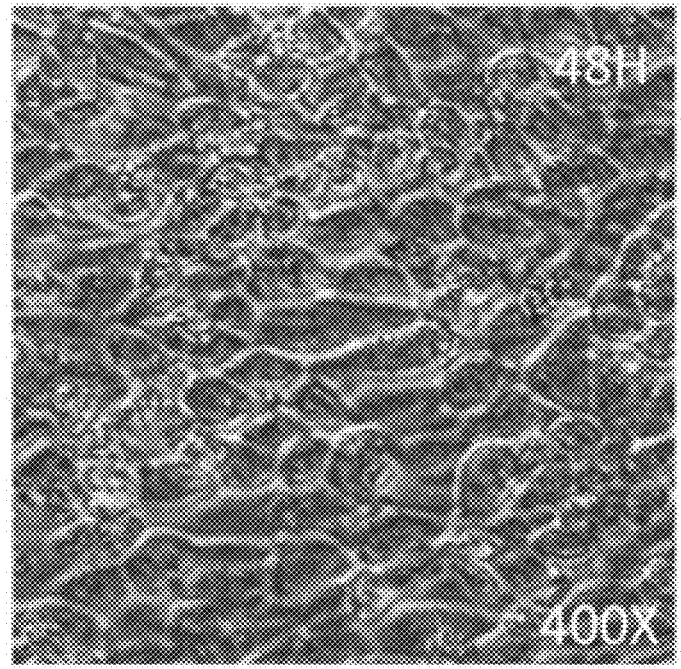
FIG. 7A shows cancer cells morphology of control HCT-116 cells.
Figure 7B:
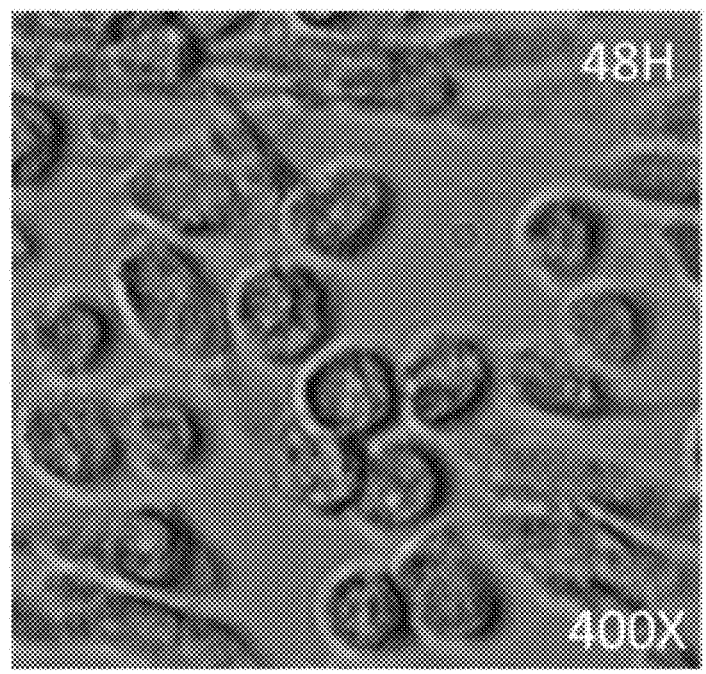
FIG. 7B shows cancer cells morphology of HCT-116 after 48 hours of treating the cells with 100 μg/mL of BG-(ATri)$_2$.
Figure 7C:
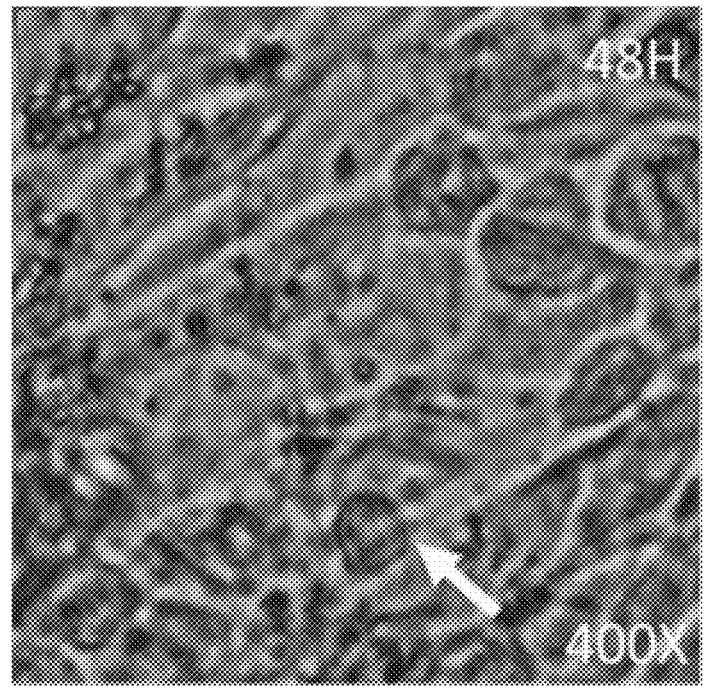
FIG. 7C shows cancer cells morphology of HCT-116 after 48 hours of treating the cells with 500 μg/mL of BG-(ATri)$_2$. The arrow points to a cancer cell nuclear condensation and augmentation at 400× magnifications.
Figure 7D:
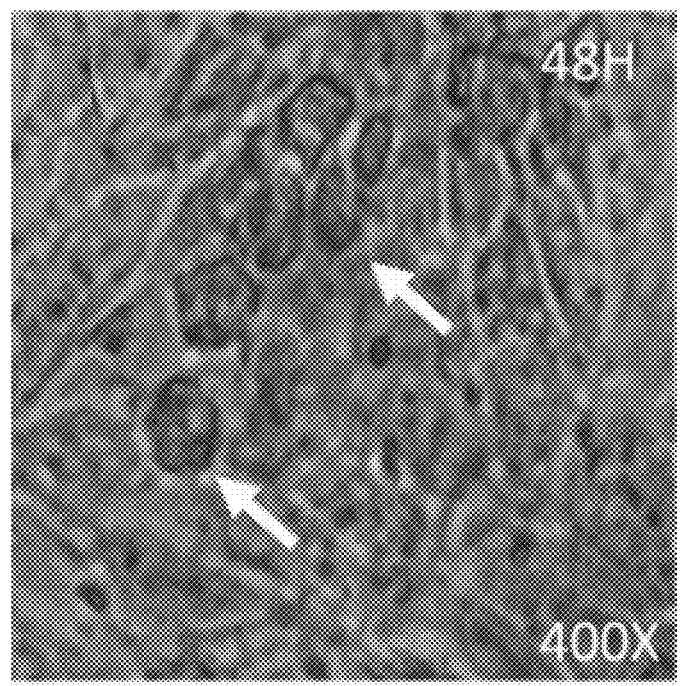
FIG. 7D shows cancer cells morphology of HCT-116 after 48 hours of treating the cells with 750 μg/mL of BG-(ATri)$_2$. The arrow points to a strong nuclear condensation and augmentation and showed the beginning of cell membrane disruption at 400× magnifications.

Effect of BG-(ATri)$_2$ on Cancer Cell Morphology:

Treatment of cells with 100 μg/mL BG-(ATri)$_2$ resulted in significant levels of nucleus condensation and nuclear augmentation of the HCT-116 cells (FIG. 7B). No morphological changes were observed in control cells (FIG. 7A). Cells treated with 500 μg/mL showed nuclear condensation and augmentation (FIG. 7C). Significant loss of cell population was observed on treatment of the cells with 750 μg/mL as large number of cancer cells were found dead (FIG. 7D).

Figure 8A:
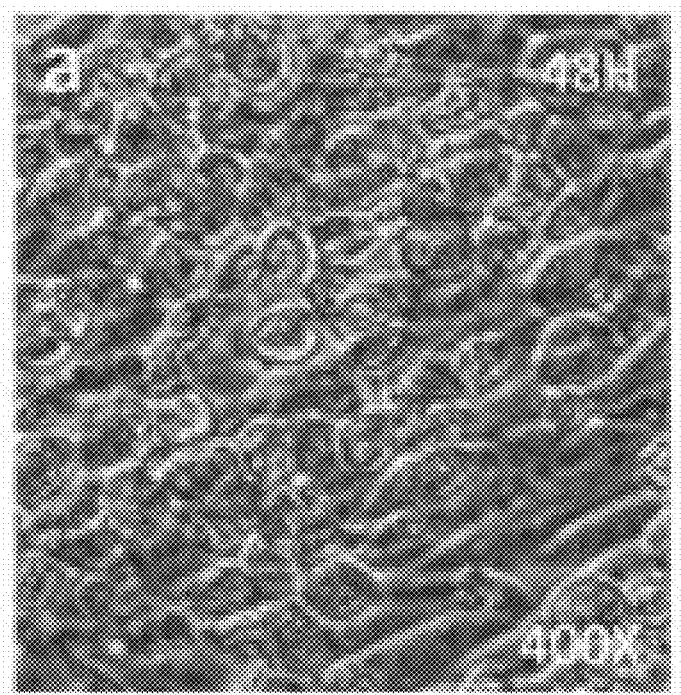
FIG. 8A shows cancer cells morphology of control HCT-116 cells.
Figure 8B:
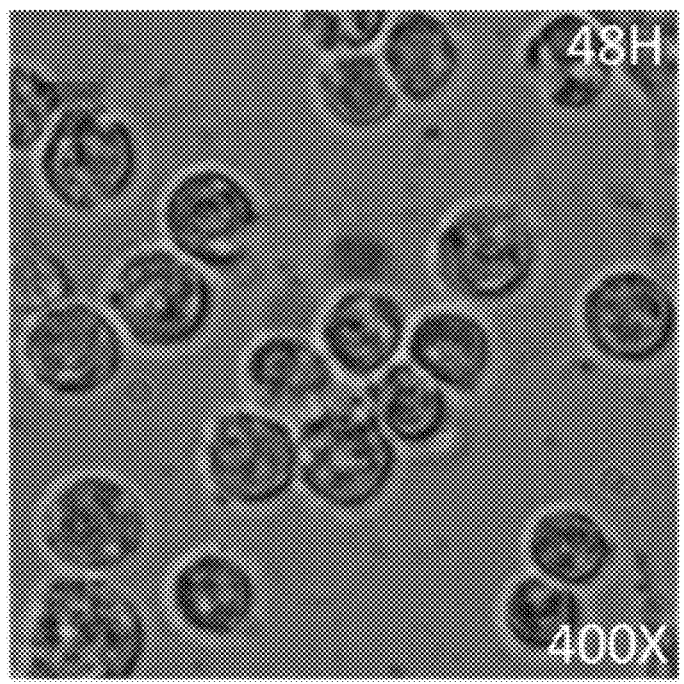
FIG. 8B shows cancer cells morphology of HCT-116 after 48 hours of treating the cells with 100 μg/mL of BG-(ATet)$_2$.
Figure 8C:
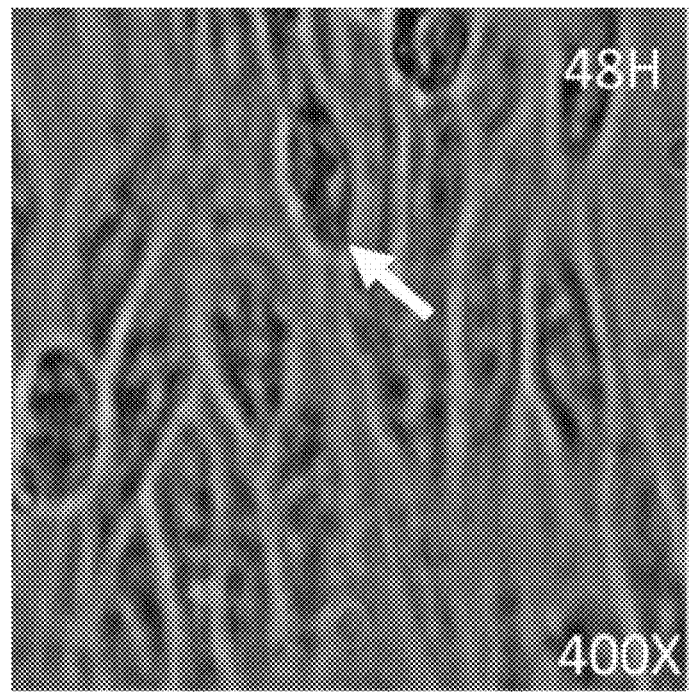
FIG. 8C shows cancer cells morphology of HCT-116 after 48 hours of treating the cells with 500 μg/mL of BG-(ATet)$_2$. The arrow points to a cancer cell nuclear condensation and augmentation at 400× magnifications.
Figure 8D:
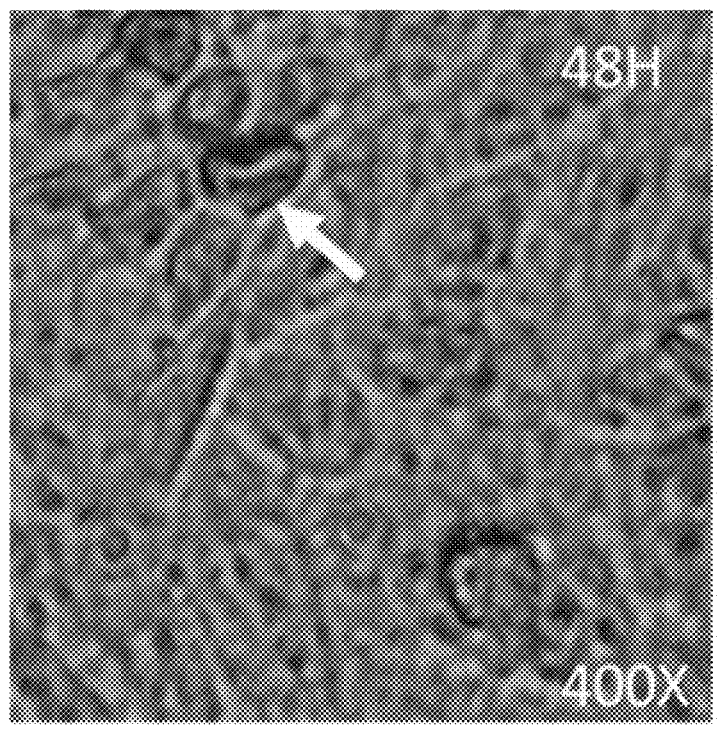
FIG. 8D shows cancer cells morphology of HCT-116 after 48 hours of treating the cells with 750 μg/mL of BG-(ATet)$_2$. The arrow points to a strong nuclear condensation and augmentation and showed the beginning of cell membrane disruption at 400× magnifications.

Effect of BG-(Atet)$_2$ on Cancer Cell Morphology:

Treatment of cells with 100 μg/mL BG-(Atet)$_2$ resulted in a strong nucleus condensation and nuclear augmentation of the cells (FIG. 8B). Control cells did not display any morphological changes (FIG. 8A). Further nucleus condensation and augmentation of cell was observed when treated with 500 μg/mL (FIG. 8C), and a significant loss of cell population resulted from treatment of the cells with of 750 μg/mL (FIG. 8D).

Figure 9A:
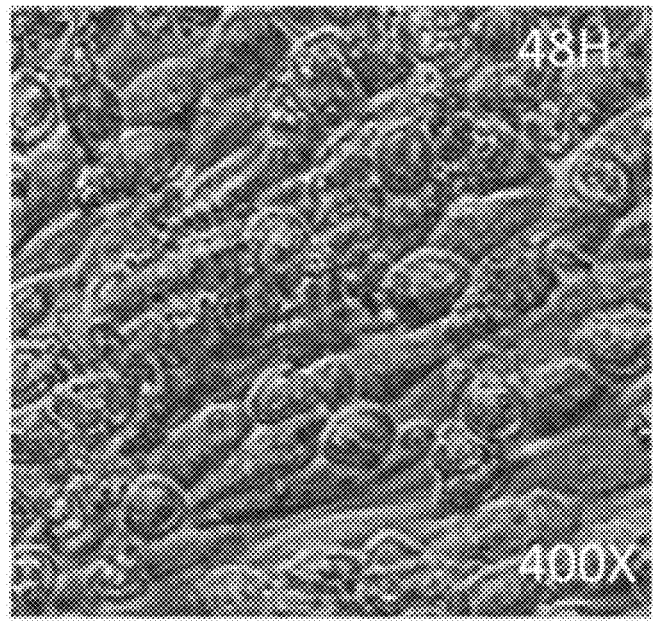
FIG. 9A shows cancer cells morphology of control HCT-116 cells.
Figure 9B:
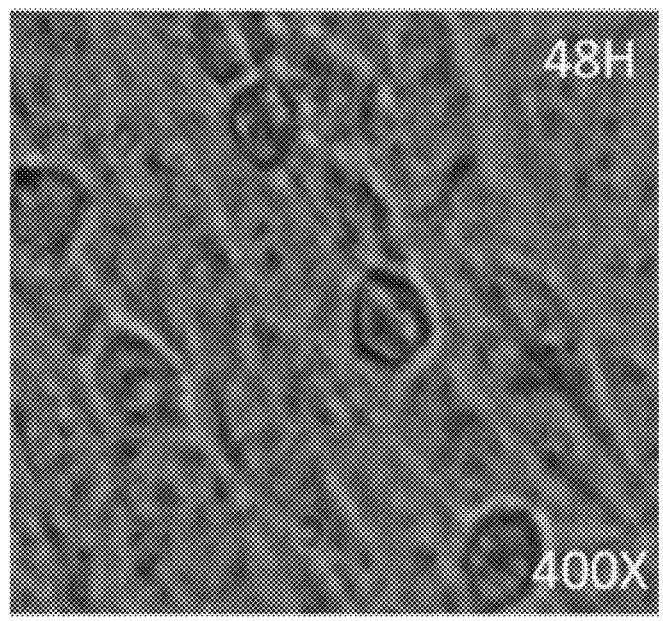
FIG. 9B shows cancer cells morphology of HCT-116 after 48 hours of treating the cells with 100 μg/mL of BG-(Imi)$_2$.
Figure 9C:
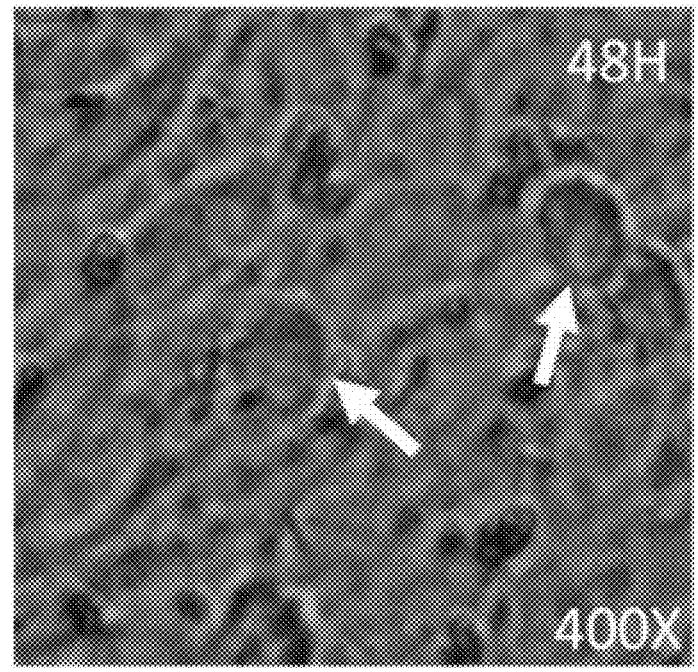
FIG. 9C shows cancer cells morphology of HCT-116 after 48 hours of treating the cells with 500 μg/mL of BG-(Imi)$_2$. The arrow points to a cancer cell nuclear condensation and augmentation at 400× magnifications.
Figure 9D:
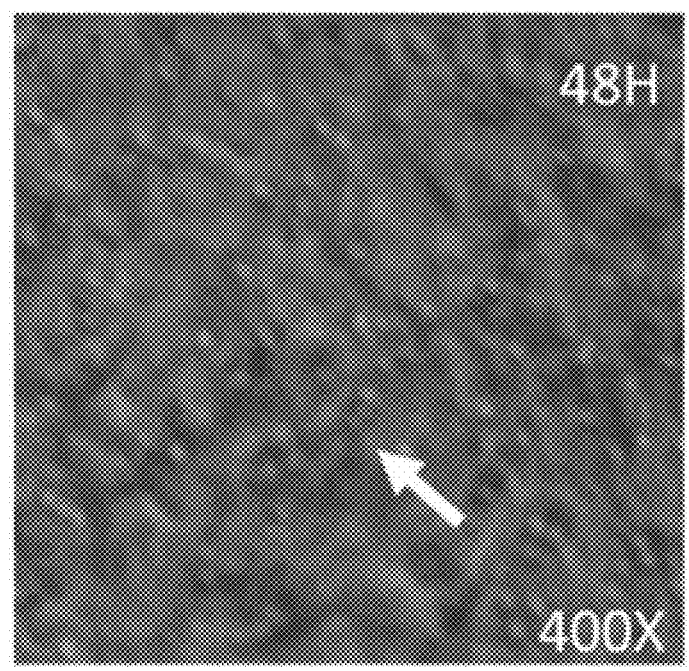
FIG. 9D shows cancer cells morphology of HCT-116 after 48 hours of treating the cells with 750 μg/mL of BG-(Imi)$_2$. The arrow points to a strong nuclear condensation and augmentation and showed the beginning of cell membrane disruption at 400× magnifications.

Effect of BG-(Imi)$_2$ on Cancer Cell Morphology:

Treatment of cells with 100 μg/mL BG-(Imi)$_2$ resulted in strong nucleus condensation and nuclear augmentation of the cells (FIG. 9B). No morphological changes were observed control cells (FIG. 9A). Cells treated with 500 μg/mL showed further nucleus condensation and augmentation (FIG. 9C), and significant loss of cell population was observed when the cells treated with 750 μg/mL showed a (FIG. 9D).

Figure 10A:
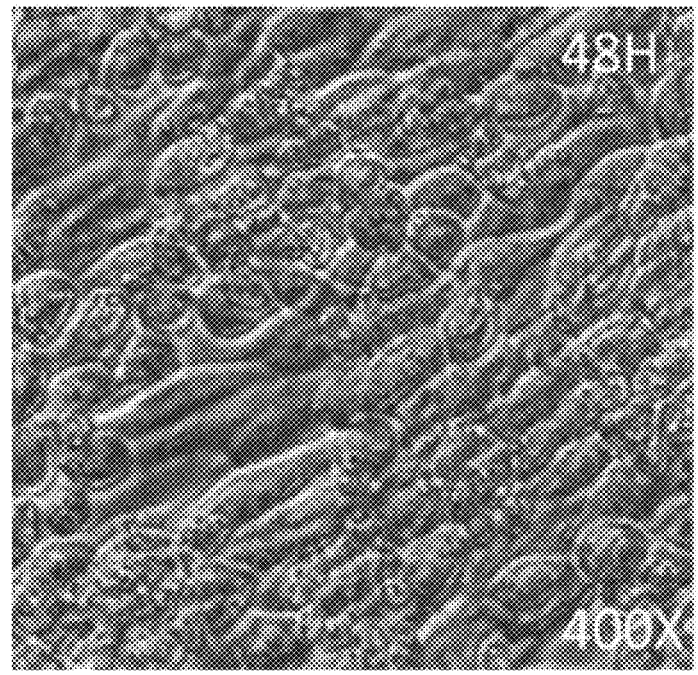
FIG. 10A shows cancer cells morphology of control HCT-116 cells.
Figure 10B:
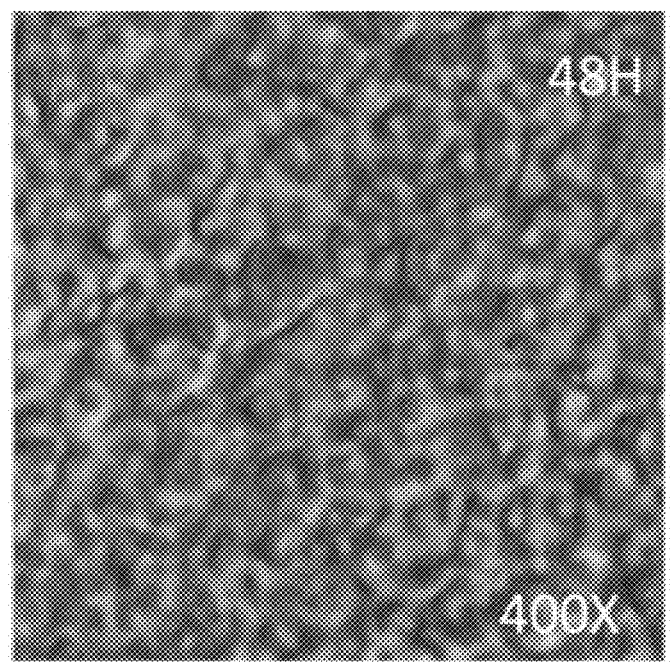
FIG. 10B shows cancer cells morphology of HCT-116 after 48 hours of treating the cells with 100 μg/mL of BG-(H$_3$PO$_4$).
Figure 10C:
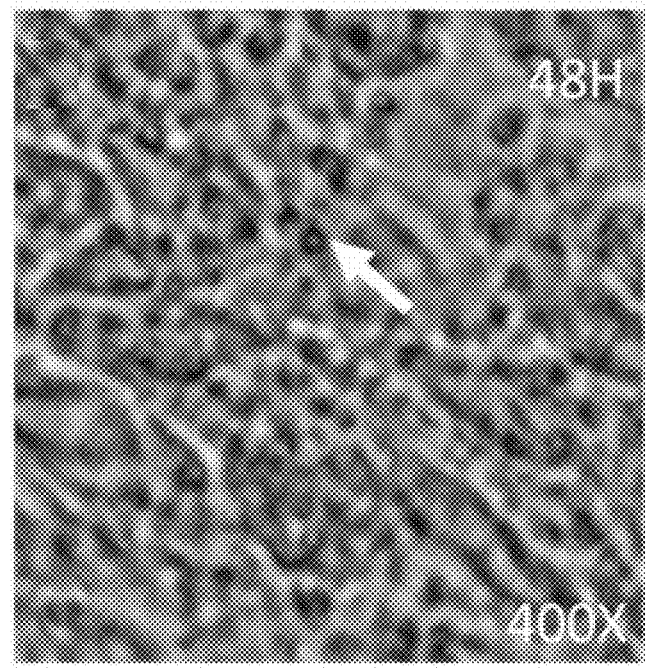
FIG. 10C shows cancer cells morphology of HCT-116 after 48 hours of treating the cells with 500 μg/mL of BG-(H$_3$PO$_4$). The arrow points to a cancer cell nuclear condensation and augmentation at 400× magnifications.
Figure 10D:
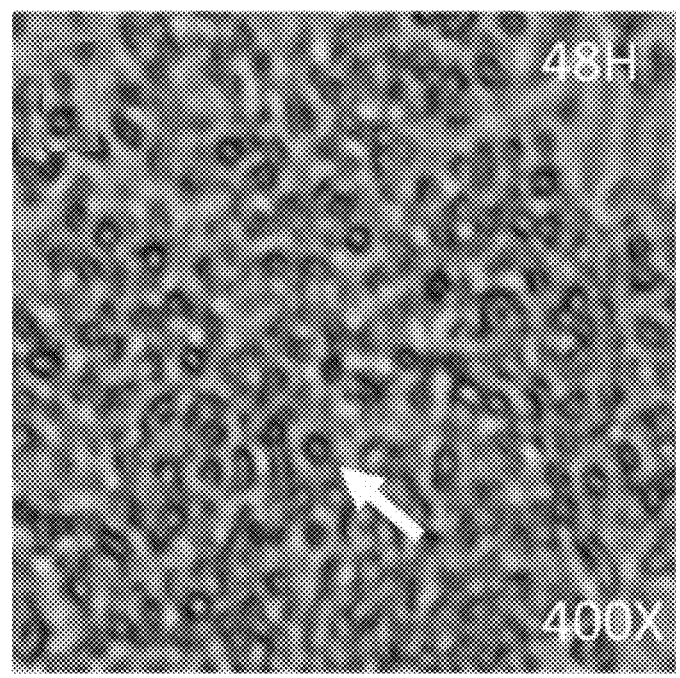
FIG. 10D shows cancer cells morphology of HCT-116 after 48 hours of treating the cells with 750 μg/mL of BG-(H$_3$PO$_4$). The arrow points to a strong nuclear condensation and augmentation and showed the beginning of cell membrane disruption at 400× magnifications.

Effect of BG-($H_3PO_4$)$_2$ on Cancer Cell Morphology:

Treatment of cells with 100 μg/mL of BG-($H_3PO_4$)$_2$ resulted in disintegrations of cancer cells (FIG. 10B) compared to control cells (FIG. 10A). On treatment of the cells with 500 μg/mL and 750 μg/mL, strong nuclear condensation and augmentation of cells were observed (FIGS. 10C; 10D).

Cancer Cells Survivability:

The HCT-116 cells were treated with BG-(Tri)$_2$, BG-(ATri)$_2$, BG-(Atet)$_2$, BG-(Imi)$_2$, and BG-($H_3PO_4$)$_2$ at a concentrations of 100 ug/mL, 500 ug/mL, and 750 ug/mL for 48 hrs. Data are the means±SD of three different experiments. Difference between two treatment groups were analysed by student's t test where (*p<0.05, p<0.01; *p<0.001), p-values were calculated by Student t-test. No changes were observed in control group. The treatments BG-(Atet)$_2$, BG-(Imi)$_2$, BG-(Tri)$_2$, and BG-(ATri)$_2$ showed most profound effects on the cancer cells compared to BG-($H_3PO_4$).

Figure 11:
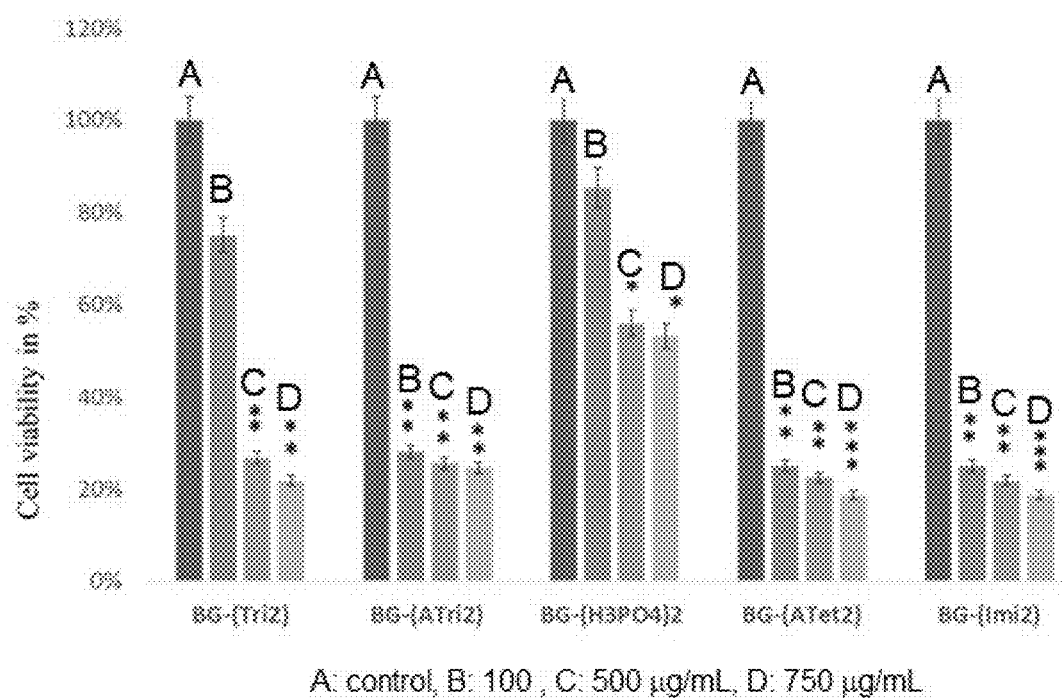
FIG. 11 shows cancer cell viability by MTT Assay.

MTT assays were carried out to examine cell viability and inhibition rate of HCT-116 cells growth. Different concentrations of BG-(Tri)$_2$, BG-(ATri)$_2$, BG-($H_3PO_4$)$_2$, BG-(Atet)$_2$, and BG-(Imi)$_2$ were used and the cultures were maintained for 48 hrs (FIG. 11). The cells viability was calculated for each sample. Cells treated with 100 ug/mL showed 75%, 28.12%, 85.31%, 25% and 25% cancer cell viability, respectively. Treatment of cells with 500 ug/mL resulted in 26.86%, 25.62%, 55.93%, 22.50% and 21.87%, respectively, cell viability. When cancer cells were treated with 750 ug/mL, cell viability decreased to 21.87%, 24.68%, 53.12%, 18.75%, and 18.75%, respectively. The most profound effect was observed with 750 ug/mL (BG-(Imi)$_2$, where cancer cells survivability was decreased by 25%, 21.87% and 18.75% respectively.

BG-(Tri)2, BG-(ATri)2, BG-(Atet)2, BG-(Imi)2, BG-(H3PO4)2 have profound effects on cancer cells survivability. The microscopic evaluation of both control and BG-azoles treated cancer cells showed that BG-(Tri)$_2$, BG-(ATri)$_2$, BG-(Atet)$_2$, BG-(Imi)$_2$, BG-(H$_3$PO$_4$)$_2$ not only affected the cancer cell membrane, but also induced nuclear condensation, augmentation and disintegration. This first is first report where BG-azole conjugates have been tested on human cancer cells. Previously, several reports have shown that azole and their derivatives possess anti-cancer properties (Kaur et al., 2016; Soares et al., 2013; Wang et al.; Khaybullin et al.; Jabir et al.; Duan et al.; and Kumar et al.). Human colorectal carcinoma cells (HCT-116) were used to evaluate anti-cancer properties of BG-(Tri)$_2$, BG-(ATri)$_2$, BG-(Atet)$_2$, and BG-(Imi)$_2$ respectively. HCT-116 cells have been widely used for testing anti-cancer drugs [Sudeep et al. (2018) "Standardized Withania somnifera Root Extract Induces Apoptosis in Murine Melanoma Cells" Pharmacogn Mag. (Suppl 4):S801-S806. doi: 10.4103/pm.pm_121_17. Epub 2018 Jan. 31. PMID: 29491636; Mazewski et al. (2018) "Comparison of the effect of chemical composition of anthocyanin-rich plant extracts on colon cancer cell proliferation and their potential mechanism of action using in vitro, in silico, and biochemical assays" Food Chem. 2018 Mar. 1; 242:378-388. doi: 10.1016/j.foodchem.2017.09.086. Epub 2017 Sep. 18. PMID: 2903770; Matsuoka et al. (2018) "Effective Sequential Combined Chemotherapy with Trifluridine/Tipiracil and Regorafenib in Human Colorectal Cancer Cells" Int J Mol Sci. 2018 Sep. 25; 19(10). pii: E2915. doi: 10.3390/ijms19102915; Li, J. J. (2015) Top Drugs: History, Pharmacology, Syntheses. Oxford University Press, 2015; Zheng et al. (2017) "miR-378 suppresses the proliferation, migration and invasion of colon cancer cells by inhibiting SDAD1" Cell Mol Biol Lett. 2017 Jul. 17; 22:12. doi: 10.1186/s11658-017-0041-5. eCollection 2017. PMID: 28725241; Sinha et al. (2017) Induction of apoptosis in human colorectal cancer cell line, HCT-116 by a vanadium-Schiff base complex. Biomed Pharmacother. 2017 August; 92:509-518. doi: 10.1016/j.biopha.2017.05.108. Epub 2017 May 30. PMID: 28575808; and Khan et al. "Fluorescent magnetic submicronic polymer (FMSP) nanoparticles induce cell death in human colorectal carcinoma cells" Artif Cells Nanomed Biotechnol. 2018 Jul. 25:1-7. doi: 10.1080/21691401.2018.1491476].

Among all five BG-azoles which have been tested, BG-(Tri)$_2$, BG-(ATri)$_2$, BG-(Atet)$_2$, and BG-(Imi)$_2$ are highly effective in attenuating cancer cells proliferation. BG-(Tri)$_2$, BG-(ATri)$_2$, BG-(Atet)$_2$, BG-(Imi)$_2$, BG-(Tri)$_2$ (1,2,4-Triazole) are more effective than BG-(H$_3$PO$_4$)$_2$ in attenuating cancer cells proliferation. It has been reported that 1,2,4-triazole has anti-inflammatory and anti-proliferative characteristics against cancer cells (Tahlan et al. 2017). The main characteristics of 1,2,4-triazole is that it is water soluble and flexible, and has the potential to interact with some enzymes involved in cancer development (Aliabadi et al., 2016). Furthermore, the existence of a triazole ring brings higher liver microsomal stability (such as liver membrane stability) and anti-cancer properties. Also, 1,2,4-triazole derivatives possess strong anti-proliferative agents against cancer cell lines (Qin et al., 2014). Other azole compounds such as 3-aminotriazole, 5-aminotetrazole, amidazole have been reported to have anti-cancer activities (Liu et al. 2010; Serebryanskaya et al. 2013; Dvořák et al. 2012).

The results presented herein shows that BG-(Tri)$_2$, BG-(ATri)$_2$, BG-(Atet)$_2$, BG-(Imi)$_2$, BG-(H$_3$PO$_4$)$_2$ showed dose dependent effects on cancer cell survivability (FIG. 11). Similar results were reported when cancer cells treated with fluorescent magnetic submicronic polymer nanoparticles (FMSP-nanoparticles) and the cell survivability displayed dose-dependent response (Khan et al. 2018).

The invention claimed is:

1. A compound having the chemical structure of formula I:

Formula I

Azole–⟨structure⟩–OH / HO–⟨structure⟩–Azole wherein the azole is selected from the group consisting of:

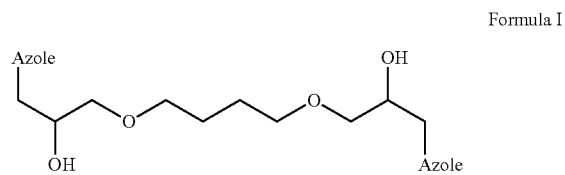

, and wherein $R_2$, $R_3$, $R_4$, $R_5$, $R_6$, $R_7$, $R_8$, $R_9$, $R_{10}$, and $R_{11}$ are independently selected from the group consisting of a hydrogen, $NR_{12}R_{13}$, $OR_{12}$, $SR_{12}$, $SeR_{12}$, an optionally substituted alkyl, an optionally substituted alkylene, an optionally substituted cycloalkyl, an optionally substituted aryl, and an optionally substituted arylalkyl; and $R_{12}$ and $R_{13}$ are independently hydrogen, an optionally substituted alkyl, an optionally cycloalkyl, an optionally substituted heterocyclyl, an optionally substituted aryl, and an optionally substituted arylalkyl; or $R_2$ and $R_3$, $R_7$ and $R_8$, or $R_9$ and $R_{10}$ are linked together forming an optionally substituted ring selected from the group consisting of a five membered ring, a six membered ring, a seven membered ring, or an eight membered ring.

2. A pharmaceutical composition comprising the compound of claim 1, and a pharmaceutically acceptable carrier and/or excipient.

3. The pharmaceutical composition of claim 2, which comprises 0.1-400 μM of the compound relative to the total volume of the composition.

4. The pharmaceutical composition of claim 2, wherein the pharmaceutically acceptable carrier and/or excipient is at least one selected from the group consisting of a buffer, an inorganic salt, a fatty acid, a vegetable oil, a synthetic fatty ester, a surfactant, and a polymer.

5. The pharmaceutical composition of claim 2, further comprising at least one chemotherapeutic agent.

6. A method of treating a cancer, comprising:
administering to a subject in need of treatment for the cancer a sufficient amount of the pharmaceutical composition of claim 2,
wherein the amount is sufficient to reduce the cancer, inhibit the progression of the cancer, reduce the severity of one or more symptoms of the cancer, or ameliorate one or more symptoms of the cancer.

7. The method of claim 6, wherein the cancer is at least one selected from the group consisting of ovarian cancer, cervical cancer, testicular cancer, colon cancer, rectal cancer, bladder cancer, breast cancer, non-small cell lung cancer, esophageal cancer, endometrial cancer, head and neck cancer, and osteogenic sarcoma.

8. The method of claim 6, wherein the subject is a mammal.

* * * * *